US011779270B2

(12) United States Patent
Ben-Kiki et al.

(10) Patent No.: US 11,779,270 B2
(45) Date of Patent: Oct. 10, 2023

(54) SYSTEMS AND METHODS FOR TRAINING ARTIFICIALLY-INTELLIGENT CLASSIFIER

(71) Applicant: Happify, Inc., New York, NY (US)

(72) Inventors: Tomer Ben-Kiki, New York, NY (US); Ran Zilca, Ra'anana (IL); Derrick Carpenter, Middletown, CT (US)

(73) Assignee: TWILL, INC., New York, NY (US)

(*) Notice: Subject to any disclaimer, the term of this patent is extended or adjusted under 35 U.S.C. 154(b) by 662 days.

(21) Appl. No.: 16/059,498

(22) Filed: Aug. 9, 2018

(65) Prior Publication Data

US 2018/0344242 A1 Dec. 6, 2018

Related U.S. Application Data

(63) Continuation-in-part of application No. 16/032,344, filed on Jul. 11, 2018, now Pat. No. 10,813,584, and
(Continued)

(51) Int. Cl.
*G06F 40/30* (2020.01)
*G06V 30/40* (2022.01)
(Continued)

(52) U.S. Cl.
CPC ............ *A61B 5/4833* (2013.01); *A61B 5/165* (2013.01); *A61B 5/486* (2013.01); *A61B 5/7425* (2013.01);
(Continued)

(58) Field of Classification Search
None
See application file for complete search history.

(56) References Cited

U.S. PATENT DOCUMENTS

| 5,435,324 A | 7/1995 | Brill |
|---|---|---|
| 5,722,418 A | 3/1998 | Bro |

(Continued)

FOREIGN PATENT DOCUMENTS

| CN | 101799849 A | 8/2010 |
|---|---|---|
| CN | 102933136 A | 2/2013 |

(Continued)

OTHER PUBLICATIONS

"LSUN: Construction of a Large-Scale Image Dataset using Deep Learning with Humans in the Loop", by Yu et al., Princeton University. (Year: 2016).*

(Continued)

*Primary Examiner* — Backhean Tiv
*Assistant Examiner* — Jonathan A Sparks
(74) *Attorney, Agent, or Firm* — Bochner PLLC; Andrew D. Bochner

(57) ABSTRACT

A computing system/method for enabling a user to improve, via training, a system designed to increase the emotional and/or physical well-being of persons, or designed for other purposes. The system/method includes retrieving a user response from a dialogue database, the user response having already labeled thereto an assigned class having a highest confidence score, the confidence score indicating degree of confidence that context of the retrieved user response is of the assigned class, displaying, the assigned class, along with other classes each having a respective lower confidence score, and receiving an indication of validity of the assigned class. The system/method further includes retrieving of a pair of sequential user response and follow-up prompt from the database, displaying user-selectable ratings, each rating designating a respectively different quality to the follow-up prompt, receiving selection of a rating and a related com-
(Continued)

ment, and associating the selection and the comment to the follow-up prompt.

14 Claims, 18 Drawing Sheets

Related U.S. Application Data a continuation-in-part of application No. 15/974,978, filed on May 9, 2018, now abandoned, which is a continuation-in-part of application No. 14/990,380, filed on Jan. 7, 2016, now abandoned, which is a continuation-in-part of application No. 14/284,229, filed on May 21, 2014, now abandoned.

(60) Provisional application No. 62/656,231, filed on Apr. 11, 2018, provisional application No. 62/533,423, filed on Jul. 17, 2017, provisional application No. 62/101,315, filed on Jan. 8, 2015, provisional application No. 61/825,742, filed on May 21, 2013.

(51) Int. Cl.
| | |
|---|---|
| A61B 5/00 | (2006.01) |
| A61M 21/02 | (2006.01) |
| G10L 15/22 | (2006.01) |
| A61B 5/16 | (2006.01) |
| G10L 25/63 | (2013.01) |
| A61M 21/00 | (2006.01) |

(52) U.S. Cl.
CPC ............ *A61M 21/02* (2013.01); *G06F 40/30* (2020.01); *G10L 15/22* (2013.01); *G10L 25/63* (2013.01); *A61B 5/4836* (2013.01); *A61M 2021/005* (2013.01); *A61M 2021/0027* (2013.01); *A61M 2205/3303* (2013.01); *A61M 2205/3375* (2013.01); *A61M 2205/3553* (2013.01); *A61M 2205/3584* (2013.01); *A61M 2205/502* (2013.01); *A61M 2205/505* (2013.01); *A61M 2205/52* (2013.01); *A61M 2230/50* (2013.01); *A61M 2230/63* (2013.01); *G06V 30/43* (2022.01); *G10L 2015/227* (2013.01)

(56) References Cited

U.S. PATENT DOCUMENTS

| | | | |
|---|---|---|---|
| 6,293,904 | B1 | 9/2001 | Blazey et al. |
| 6,728,679 | B1 | 4/2004 | Strubbe et al. |
| 7,644,060 | B2 | 1/2010 | Kadri |
| 8,577,671 | B1 | 11/2013 | Barve et al. |
| 9,302,179 | B1 | 4/2016 | Merzenich et al. |
| 9,754,308 | B2* | 9/2017 | Pinckney ........... G06Q 30/0631 |
| 2003/0059750 | A1 | 3/2003 | Bindler et al. |
| 2005/0228691 | A1 | 10/2005 | Paparo |
| 2007/0143281 | A1 | 6/2007 | Smirin et al. |
| 2008/0091705 | A1* | 4/2008 | McBride ................ G06Q 50/10 |
| | | | 707/999.102 |
| 2009/0037470 | A1 | 2/2009 | Schmidt |
| 2009/0119234 | A1 | 5/2009 | Pinckney et al. |
| 2009/0171902 | A1 | 7/2009 | MacLaurin et al. |
| 2010/0004995 | A1* | 1/2010 | Hickman ................ G06F 3/14 |
| | | | 705/14.58 |
| 2010/0218118 | A1 | 8/2010 | Bronkema |
| 2011/0125844 | A1 | 5/2011 | Collier et al. |
| 2011/0183305 | A1 | 7/2011 | Orbach |
| 2012/0095862 | A1 | 4/2012 | Schiff et al. |
| 2012/0238800 | A1 | 9/2012 | Naujokat et al. |
| 2012/0246102 | A1 | 9/2012 | Sudharsan |
| 2012/0315613 | A1 | 12/2012 | Shatte et al. |
| 2013/0101970 | A1 | 4/2013 | Mascarenhas |
| 2013/0144605 | A1* | 6/2013 | Brager .................. G06F 40/40 |
| | | | 704/9 |
| 2013/0216989 | A1 | 8/2013 | Cuthbert |
| 2014/0032234 | A1 | 1/2014 | Anderson |
| 2014/0157171 | A1 | 6/2014 | Brust et al. |
| 2014/0212853 | A1 | 7/2014 | Divakaran et al. |
| 2014/0223462 | A1 | 8/2014 | Aimone et al. |
| 2014/0274413 | A1 | 9/2014 | Chelst |
| 2014/0276244 | A1 | 9/2014 | Kamyar |
| 2014/0351332 | A1 | 11/2014 | Ben-Kiki et al. |
| 2015/0140527 | A1 | 5/2015 | Gilad-Barach et al. |
| 2015/0199010 | A1 | 7/2015 | Coleman et al. |
| 2015/0199913 | A1* | 7/2015 | Mayfield ................ G09B 7/02 |
| | | | 434/353 |
| 2015/0297109 | A1 | 10/2015 | Garten et al. |
| 2015/0339363 | A1 | 11/2015 | Moldoveanu et al. |
| 2015/0348569 | A1 | 12/2015 | Allam et al. |
| 2015/0351655 | A1 | 12/2015 | Coleman |
| 2015/0371663 | A1 | 12/2015 | Gustafson et al. |
| 2016/0048772 | A1* | 2/2016 | Bruno ................... G06N 20/00 |
| | | | 706/11 |
| 2016/0055236 | A1 | 2/2016 | Frank et al. |
| 2016/0203729 | A1 | 7/2016 | Zilca |
| 2016/0217501 | A1* | 7/2016 | Brigham ................ G06N 20/00 |
| 2016/0350687 | A1 | 12/2016 | Yamamoto et al. |
| 2017/0032279 | A1 | 2/2017 | Miserendino et al. |
| 2017/0125008 | A1 | 5/2017 | Maisonnier et al. |
| 2017/0169531 | A1 | 6/2017 | Lycas |
| 2017/0345324 | A1 | 11/2017 | Fanty et al. |
| 2018/0075368 | A1 | 3/2018 | Brennan et al. |
| 2018/0108353 | A1 | 4/2018 | Gustafson et al. |
| 2018/0260387 | A1 | 9/2018 | Ben-Kiki et al. |
| 2018/0317840 | A1 | 11/2018 | Ben-Kiki et al. |
| 2018/0344242 | A1 | 12/2018 | Ben-Kiki et al. |
| 2019/0156358 | A1* | 5/2019 | Pace .................. G06Q 30/0203 |
| 2020/0034421 | A1* | 1/2020 | Ferrucci ................. G10L 15/26 |
| 2020/0099740 | A1 | 3/2020 | Ben-Kiki et al. |

FOREIGN PATENT DOCUMENTS

| | | |
|---|---|---|
| CN | 103400054 A | 11/2013 |
| WO | 01/22384 A1 | 3/2001 |
| WO | WO-2010144766 A1 | 12/2010 |
| WO | 2012/094516 A1 | 7/2012 |
| WO | 2013/059290 A1 | 4/2013 |

OTHER PUBLICATIONS

Jerry Alan Fails and Dan R. Olsen. 2003. Interactive machine learning. In Proceedings of the 8th international conference on Intelligent user interfaces (IUI '03). Association for Computing Machinery, New York, NY, USA, 39-45. (Year: 2003).*
Canadian Office Action dated Apr. 16, 2019 for corresponding Canadian Application 2,949,605 filed Nov. 18, 2016 (4 pages).
Canadian Office Action dated Apr. 30, 2020 for corresponding Canadian Application 2949605, filed Nov. 18, 2016 (9 pages).
Chinese Office Action dated Aug. 14, 2018 in corresponding Chinese Application 201480041214.1 filed Jan. 20, 2016 (5 pages).
Chinese Office Action dated Aug. 24, 2017 in corresponding Chinese Application 201480041214.1 filed Jan. 20, 2016 (7 pages).
Chinese Office Action dated Mar. 14, 2019 in corresponding Chinese Application 201480041214.1 filed Jan. 20, 2016 (10 pages).
Chinese Office Action dated Sep. 29, 2019 in corresponding Chinese Application 201480041214.1 filed Jan. 20, 2016 (8 pages).
Mccallum, Simon "Gamification and serious games for personalized health". 2012. Publisher. Studies in health technology and informations. (Year: 2012).
International Search Report of International Application No. PCT/US2018/042272 dated Nov. 29, 2018.
Beun et al., "Improving Adherence in Automated e-Coaching", International Conference on Persuasive Technology, Persuasive 2016: Persuasive Technology pp. 276-287. (Year: 2016).
Ciaramicoli, "What is Empathic CBT", <https://web.archive.org/web/20161014010605/http://www.balanceyoursuccess.com/what-is-empathic-cbt/> (Year: 2016).

(56) References Cited

OTHER PUBLICATIONS

European Examination Report for Application No. 14801490.5 dated Oct. 22, 2019.
Nov. 23, 2016 European Search Report, which is enclosed, that issued in European Patent Application No. 14801490.5.
International Search Report dated Nov. 6, 2014, which is enclosed, that issued in the corresponding European Patent Application No. PCT/US2014/039022.
International Search Report and Written Opinion for International Application No. PCT/US2019/036972 dated Sep. 23, 2019.
International Preliminary Report on Patentability for International Application No. PCT/US2018/041603 dated Jan. 21, 2020.
International Preliminary Report on Patentability for International Application No. PCT/US2018/042272 dated Jan. 30, 2020.
International Search Report of International Application No. PCT/US2018/041603 dated Nov. 8, 2018, which is enclosed.
"Greenolive: an Open Platform for Wellness Management Ecosystem", by Zeng et al., 2010 (Year: 2010).
International Search Report and Written Opinion for International Application No. PCT/US2020/053820 dated Jan. 14, 2021.
European Search Report for Application No. 18835919.4 dated Mar. 15, 2021.
European Search Report for Application No. 18835438.5 dated Mar. 15, 2021.
U.S. Appl. No. 17/494,407, filed Oct. 5, 2021, Tomer Ben-Kiki.
U.S. Appl. No. 17/510,341, filed Oct. 25, 2021, Ran Zilca.
U.S. Appl. No. 17/671,251, filed Feb. 14, 2022, Tomer Ben-Kiki.
U.S. Appl. No. 17/060,831, filed Oct. 1, 2020, Ran Zilca.
European Search Report for European Application No. 19847959.4 dated Mar. 25, 2022.

\* cited by examiner

SYSTEMS AND METHODS FOR TRAINING ARTIFICIALLY-INTELLIGENT CLASSIFIER

CROSS-REFERENCE TO RELATED APPLICATIONS

This application is a continuation-in-part of U.S. Non-Provisional application Ser. No. 16/032,344, filed on Jul. 11, 2018, which claims priority under 35 U.S.C. § 119(e) to U.S. Provisional Application Ser. No. 62/533,423, filed on Jul. 17, 2017. This application is also a continuation-in-part of U.S. Non-Provisional application Ser. No. 15/974,978, filed on May 9, 2018, which claims priority under 35 U.S.C. § 119(e) to U.S. Provisional Application Ser. Nos. 62/656,231, filed on Apr. 11, 2018 and 62/533,423, filed on Jul. 17, 2017. This application is also a continuation-in-part of U.S. Non-Provisional application Ser. No. 14/990,380, filed on Jan. 7, 2016, which claims priority under 35 U.S.C. § 119(e) to U.S. Provisional Application Ser. No. 62/101,315, filed on Jan. 8, 2015. This application is also a continuation-in-part of U.S. Non-Provisional application Ser. No. 14/284,229, filed on May 21, 2014, which claims priority under 35 U.S.C. § 119(e) to U.S. Provisional Application Ser. No. 61/825,742, filed on May 21, 2013. The entire contents of each above-noted application is herein incorporated by reference in their entirety.

FIELD OF INVENTION

The present invention is directed to a training software, and a computing system executing the training software, for training a computing system that provides an interactive environment between the computing system and a human user, for the purpose of increasing emotional and/or physical well-being of the user.

BACKGROUND

There are a multitude of programs designed to improve physical, emotional and/or psychological well-being of a person. These programs are offered through a number of channels, ranging from live in-person classes or sessions to online/offline media. Software applications executed on a mobile device (mobile applications) such as a smartphone have been developed to likewise engage users to improve their physical and/or psychological well-being. Some mobile applications employ an interactive model that adapts to a user's behavior over time and seek to serve as "virtual coaches" or "virtual psychotherapists" that guide the user to achieve a desired goal.

Some of these mobile applications also employ natural language processings to gain a better understanding of the user's reactions and/or responses. The accuracy of these mobile applications lies solely on the programming of such software and, as such, there is a need for a human administrator to review and run diagnostics in order to optimize performances of one or more features of these mobile applications.

OBJECTS AND SUMMARY OF THE INVENTION

In view of the foregoing, it is an object of the present invention to provide a training software, executable on a computing system, that provides an environment in which a human administrator can train and optimize performances of a computing system that provides an interactive environment between the computing system and a human user, for the purpose of increasing emotional and/or physical well-being of the user.

In accordance with an embodiment of the present invention, a computing system having a user-interface display screen, at least one processor, and at least one memory storing executable software is provided, in which the computing system accesses a database of dialogues, the dialogues including a plurality of computer-generated prompts and user responses, retrieves, from the database, at least one user response having already labeled thereto an assigned class having a highest confidence score, the confidence score indicating a degree of confidence that a context of the at least one retrieved user response is of the assigned class, displays, on the user-interface display screen, the assigned class, along with a plurality of other classes, each of the plurality of other classes having a respective lower confidence score, and receives, from a user of the training software, an indication of validity of the assigned class of the at least one retrieved user response. In accordance with this embodiment, each of the confidence scores is pre-determined by a natural language classifier employed to analyze the at least one user response.

As an aspect of this embodiment, the indication of validity comprises at least one of: (a) a confirmation that the assigned class is correct; and (b) a selection of one of the plurality of other classes, and when the indication of validity comprises the selection of the one of the plurality of classes, the computing system updates the assigned class of the at least one retrieved user response with the selected one of the plurality of other classes to generate an updated user response.

As a feature of this aspect, when indication of validity comprises the selection of the one of the plurality of classes, the computing system stores the updated user response as new data to the database.

As another feature of this aspect, the database with the new data is configured to be used to re-train the natural language classifier.

As another aspect, the at least one retrieved user response has pre-associated therewith the assigned class with the highest confidence score and the plurality of other classes with the respective lower confidence score.

As yet another aspect, the dialogues stored in the database are configured to be from a series of interactions between an interactive computing system and a user of the interactive computing system.

As a feature of this aspect, the series of interactions are a set of activities designed to cause an increase in a level of happiness of the user of the interactive computing system.

In accordance with another embodiment of the present invention, a method comprises accessing a database of dialogues, the dialogues including a plurality of computer-generated prompts and user responses, retrieving, from the database, at least one user response having already labeled thereto an assigned class having a highest confidence score, the confidence score indicating a degree of confidence that a context of the at least one retrieved user response is of the assigned class, displaying, on a user-interface display screen, the assigned class, along with a plurality of other classes, each of the plurality of other classes having a respective lower confidence score, and receiving an indication of validity of the assigned class of the at least one retrieved user response. In accordance with this method, each of the confidence scores is pre-determined by a natural language classifier employed to analyze the at least one user response.

As an aspect of this embodiment, the indication of validity comprises at least one of: (a) a confirmation that the assigned class is correct; and (b) a selection of one of the plurality of other classes, and when the indication of validity comprises the selection of the one of the plurality of classes, the method further comprises updating the assigned class of the at least one retrieved user response with the selected one of the plurality of other classes to generate an updated user response.

As a feature of this aspect, when indication of validity comprises the selection of the one of the plurality of classes, the method further comprises storing the updated user response as new data to the database.

As another feature of this aspect, the database with the new data is configured to be used to re-train the natural language classifier.

As another aspect, the at least one retrieved user response has pre-associated therewith the assigned class with the highest confidence score and the plurality of other classes with the respective lower confidence scores.

As yet another aspect, the dialogues stored in the database are configured to be from a series of interactions between an interactive computing system and a user of the interactive computing system.

As a feature of this aspect, the series of interactions are a set of activities designed to cause an increase in a level of happiness of the user of the interactive computing system.

In accordance with yet another embodiment of the present invention, a computing system having a user-interface display screen, at least one processor, and at least one memory storing executable training software is provided, in which the computing system accesses a database of dialogues, the dialogues including a plurality of user responses and computer-generated prompts, retrieves, from the database, at least one pair of sequential user response and follow-up computer-generated prompt, displays, on the user-interface display screen, a plurality of user-selectable ratings, each of the ratings designating a respectively different quality to the retrieved follow-up computer-generated prompt, receive, from a user of the training software, a selection of one of the plurality of user-selectable ratings, and receive, from the user of the training software, a comment regarding the selected user-selectable rating. The computing system further associates the selected user-selectable rating and the comment regarding the selected user-selectable rating to the retrieved follow-up computer-generated prompt.

As an aspect of this embodiment, the dialogues stored in the database are from a series of interactions between an interactive computing system and a user of the interactive computing system.

As a feature of this aspect, the series of interactions are a set of activities designed to cause an increase in a level of happiness of the user of the interactive computing system.

As another feature of this aspect, the computing system generates a record of associating the selected user-selectable rating and the comment regarding the selected user-selectable rating to the retrieved follow-up computer-generated prompt, and the record is configured to be used to re-format a flow of a future interaction between the interactive computing system and the user of the interactive computing system.

As another aspect, the plurality of user-selectable ratings include at least one of exceptional, good, excessive, insufficient and out of context.

As a feature of this aspect, the quality is indicative of a level of emotional intelligence conveyed by the retrieved follow-up computer-generated prompt.

In accordance with a further embodiment, a method comprises accessing a database of dialogues, the dialogues including a plurality of user responses and computer-generated prompts, retrieving, from the database, at least one pair of sequential user response and follow-up computer-generated prompt, displaying, on a user-interface display screen, a plurality of user-selectable ratings, each of the ratings designating a respectively different quality to the retrieved follow-up computer-generated prompt, receiving a selection of one of the plurality of user-selectable ratings, receiving a comment regarding the selected user-selectable rating, and associating the selected user-selectable rating and the comment regarding the selected user-selectable rating to the retrieved follow-up computer-generated prompt.

As an aspect of this embodiment, the dialogues stored in the database are from a series of interactions between an interactive computing system and a user of the interactive computing system.

As a feature of this aspect, the series of interactions are a set of activities designed to cause an increase in a level of happiness of the user of the interactive computing system.

As another feature of this aspect, the method comprises generating a record of associating the selected user-selectable rating and the comment regarding the selected user-selectable rating to the retrieved follow-up computer-generated prompt, and using the record to re-format a flow of a future interaction between the interactive computing system and the user of the interactive computing system.

As another aspect, the plurality of user-selectable ratings include at least one of exceptional, good, excessive, insufficient and out of context.

As a feature of this aspect, the quality is indicative of a level of emotional intelligence conveyed by the retrieved computer-generated prompt.

These and other objects, advantages, aspects and features of the present invention are described below and/or appreciated and understood by those of ordinary skill in the art. Although specific advantages have been enumerated above, various embodiments may include some, none, or all of the enumerated advantages and other technical advantages may become readily apparent to one of ordinary skill in the art after review of the following figures and description.

DETAILED DESCRIPTION

Figure 1:
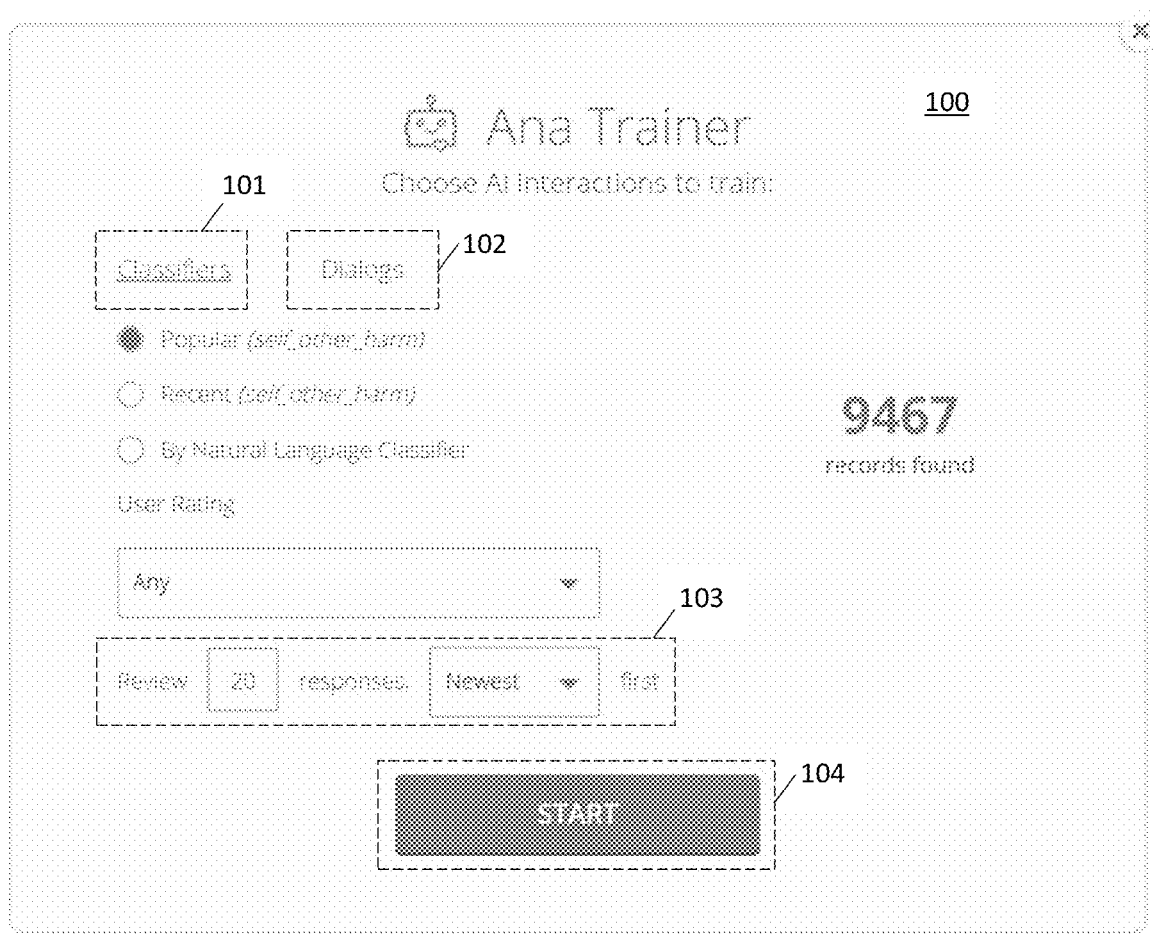
FIG. 1 is a screenshot of a start-up user-interface screen in accordance with the present invention.

The present invention is directed to a computing system that provides an interactive environment between the computing system and a human user, for the purpose of increasing emotional and/or physical well-being of the user. The interactive environment, as provided by the computing system, entails engaging the user in a series of activities and/or tasks, each particularly designed to address a specific issue or desire the user may have with respect to the user's emotional and/or physical well-being. The ultimate goal of the interaction between the computing system and the user is for the interaction to cause an increase in the user's emotional and/or physical well-being.

In accordance with the present invention, during the course of an activity, the computing system applies various natural language analytic techniques and/or algorithms to understand the nature of the user's responses and reactions. One form of the analysis technique is the use of a natural language classifier. In the present invention, the computing system may employ a number of such classifiers that analyze input data from the user, particularly the textual portion of the input data (whether spoken, written, typed or otherwise input to the computing system), in an effort to understand what the user is saying, what the user is feeling, etc. Ultimately, the computing system of the present invention gains a better understanding of the user's responses and reactions, and responds more efficiently, intelligently, and dynamically at each given moment or turn during the provided activity.

In further accordance with the present invention, the computing system may be described as being equipped with, or otherwise programmed with artificial intelligence. The term "artificial intelligence" as used herein refers to a computing system's ability to simulate a variety of human emotions and cognitive functions. As such, the computing system of the present invention may apply natural language classifiers that are trained to understand from a corpus of textual input data various indicia of emotional expressions by the user. As a result, the computing system having said artificial intelligence, responds even more emotionally intelligently (e.g., more empathetically) to the user at each given moment or turn during the activity, further causing an increased level of engagement by the user.

The above described features and benefits of a computing system in the contexts of behavioral and/or psychological health interventions have been described in greater detail in one or more of the U.S. patent applications incorporated herein by reference. More particularly, the details of such inventive computing systems and advantageous features thereof are set forth in: U.S. patent application Ser. No. 14/284,229, entitled "SYSTEMS AND METHODS FOR PROVIDING ON-LINE SERVICES"; U.S. patent application Ser. No. 14/990,380, entitled "DYNAMIC INTERACTION SYSTEM AND METHOD"; U.S. patent application Ser. No. 16/032,344, entitled "ASSESSING ADHERENCE FIDELITY TO BEHAVIORAL INTERVENTIONS USING INTERACTIVITY AND NATURAL LANGUAGE PROCESSING"; and U.S. patent application Ser. No. 15/974,978, entitled "SYSTEMS AND METHODS FOR DYNAMIC USER INTERACTION FOR IMPROVING HAPPINESS." The entire contents of each of these applications is incorporated herein by reference.

An exemplary computing system that embodies the respective inventions of the herein incorporated U.S. patent applications is referred to as "Happify" or the "Happify system." Happify is a novel, science-based online service for engaging, learning and training the skills of happiness. Happify is based on a framework developed by psychologists and researchers in a collection of therapeutic disciplines such as cognitive behavioral therapy, mindfulness, positive psychology, etc., and assists users in the development of certain skills related to being happy, for example, Savor, Thank, Aspire, Give and Empathize (or S.T.A.G.E.™). With Happify, each skill is developed using various activities, ordered in increasing skill level, that gradually unlock as the user progresses in building that skill. With Happify, a user selects a "track" that contains sets of activities that are designed to address a specific life situation or goal.

The Happify system may be implemented on a user's mobile electronic device, such as a smartphone or tablet, or may be implemented on the user's personal computer (PC). The Happify system may be embodied within a mobile application, an executable software program, or another suitable form. For instance, a user may download and install a mobile application that provides the Happify service on the user's mobile device. The user, via the mobile application, engages with Happify by selecting a Happiness track and is provided with a set of activities that are designed to improve the user's happiness level in accordance with the selected Happiness track.

The Happify system as described herein is also "artificially intelligent" in the context of behavioral health intervention. More particularly, the Happify system is artificially intelligent in the context of its interactivity with the user as the system comprises an ability to put together a conversation with the user that is empathetic, emotionally intelligent, supportive, etc. As described in the one or more of the patent applications incorporated herein, the Happify system uses dynamic topic analyses and natural language classifications on user input data to generate a prompt that conveys an understanding of the user's situation, support for the user's feelings, and empathy (and also other human cognitions) toward the user's emotion. In short, the Happify system is an emotionally intelligent behavioral health intervention service providing system.

The extent of artificial intelligence of the Happify system may be described as being based on a number of factors. For instance, the ability of the natural language classifiers of the Happify system to parse through a multifold of corpus of textual input data and to recognize trigger words necessitating formulation of an artificially intelligent response can be said to be defining the extent of artificial intelligence. Moreover, the scope of training data on which each natural language classifier makes all decisions with respect to analyzing user input data can also be said to be defining the extent of artificial intelligence. Accordingly, a particular objective of the present invention is to provide a software (e.g., a training software) that: (1) helps to optimize the accuracy of the natural language classifiers so that the best possible decisions are made at each and every turn of the interaction; and (2) continuously augments the training data with new training data so as to broaden the scope and capacity of the natural language classifiers within the Happify system. With such training software, a system administrator (also referred to herein as an "administrative user") can dive into the backbone of the Happify system and make adjustments that will improve the overall quality of the Happify service.

In the present disclosure, the term "interaction" as used herein is intended to be construed broadly. Generally, an "interaction" in the context of the present disclosure means a set of reciprocal actions between a Happify user and the Happify system. As such, an "interaction" is a performance, by a Happify user, of an activity or a task provided by the Happify system. The term "interaction" as used herein can mean a set of physical and/or verbal reciprocal actions.

In the present disclosure, the term "prompt" may be used interchangeably with the term "system prompt," or "computer generated prompt." The term "prompt" as used herein is also intended to be construed broadly. Generally, a "prompt" is a statement made by the Happify system. A "prompt" may be in the form of a command (as in instructing a Happify user to take a particular action) or in the form of a reaction (as in reacting to a Happify user's response). As described herein, prompts may be pre-generated, stored in a memory device, and accessed at appropriate times, or prompts may be generated "on the spot" using natural language synthesis techniques based on contexts of a user response.

In the present disclosure, the term "user response" is also intended to be construed broadly. Generally, a "user response" is a verbal statement made by a Happify user in response to a prompt during an activity or a task. In some embodiments, a "user response" may be referred to as user input data (or as being a component of user input data, particularly the portions of the user input data having textual or auditory data). As described herein, the Happify computing system analyzes various "user responses" by employing natural language classifiers.

Finally, in the present disclosure, the term "dialogue" or "dialog" is also intended to be construed broadly. A "dialogue" is a subset of an "interaction." Generally, a "dialogue" is a conversation between a Happify user and the Happify system. As such, a "dialogue" includes at least one prompt and at least one user statement. A "dialogue" may be referred to as a portion of verbal reciprocal actions between a Happify user and the Happify system, or it may be referred to as the entire conversation between a Happify user and the Happify system in the course of an activity or a task. Every "dialogue" between a Happify user and the Happify system during operation of the Happify system gets stored in the Happify system database and serves as training data.

In accordance with the present disclosure, one or more embodiments are set forth in which a training software described, the training software enabling a system administrator to replay dialogues from a system database, review decisions made by natural language classifiers, indicate whether a decision made is correct or incorrect, and re-train the natural language classifiers using those indications. Moreover, the training software enables the system administrator to replay every conversation and/or interaction between a Happify user and the Happify system to see how the flow of the interaction developed and why the Happify system made certain decisions, to see which computer generated prompts were delivered at which moments, to spot any discrepancy or mistake within conversations and/or interactions, and to improve computer generated prompts in order to optimize the overall flow of the Happify interactions.

The training software as described herein can be an independent executable software application, separate from the Happify system, or it may a part of, or an extension of, the main Happify system. The training software as described herein may also be a separate downloadable software that can be executed on a mobile device or on a personal computer. The training software as described herein is not intended to be available and/or otherwise readily accessible by individual Happify users. The training software as described herein is therefore generally accessible only by users with administrative access. The training software as described herein is intended to be compatible with any version of the Happify systems disclosed in the one or more patent applications incorporated herein by reference. The purpose of the Happify training software is to provide an environment in which a system administrator can create tags and labels on user input data (or modify and improve already generated tags and labels) that, in turn, can be used to train (or re-train) natural language classifiers employed by the Happify system.

Figure 8:
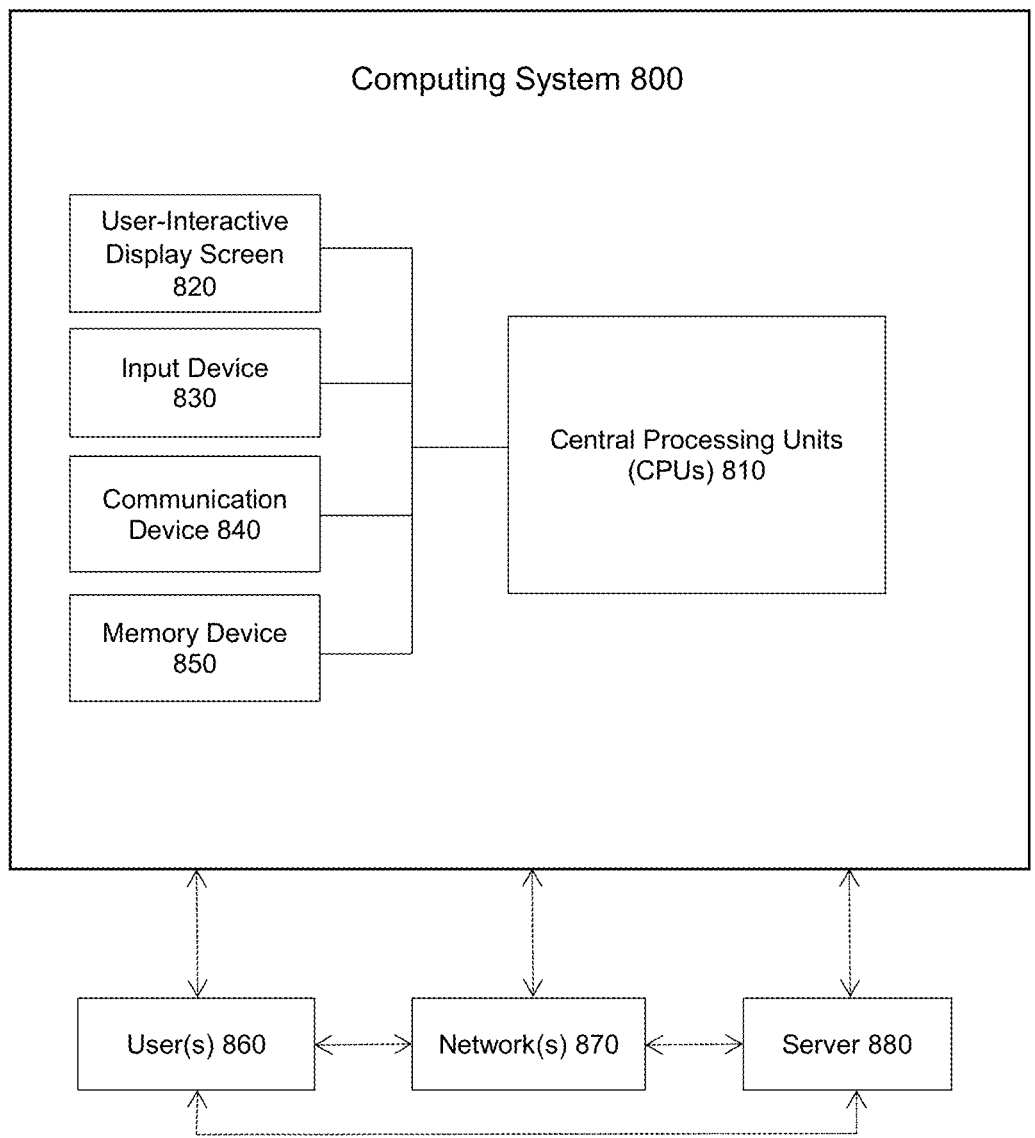
FIG. 8 is a block diagram of an exemplary computing system in accordance with the present invention.

Turning now to the drawings, in which like numerals represent the same or similar elements, an exemplary Happify training software will be described in detail. Referring first to FIG. 8, a simplified block diagram of an exemplary computing system 800 which may embody the Happify training software as described herein is shown. The computing system 800 comprises one or more central processing units (CPUs) 810, a user interface display screen 820, a communication device 840, and a memory device 850. As described herein, a user (e.g., a system administrator) operates the computing system 800 via the user-interface display screen. The input device 830 may further be used to receive input data from the user. In a case where the Happify system is embodied within the same computing device 800, the input device 830 may comprise various sensors that capture/receive user input data. The communication device 840 permits the computing system 800 to communicate with other computing systems, e.g., another computing system embodying the Happify system. The memory device 850 may store the executable training software as described herein, and may also other data.

As described herein, the CPU 810 may access, retrieve and store data to/from a database. The database may be embodied within the memory device 850 or may be a remotely located storage device (e.g., the Happify Database) accessible over a network 870 and/or a server 880. The CPU 810 also performs various other processes in accordance with the training software. In the case where the Happify system is embodied within the same computing device 800, the CPU 810 may implement various functionalities of the Happify system, such as natural language processing techniques and more. The components of the computing system 800 as described herein are only exemplary, and may further include, or not include, one or more components as disclosed in the one or more patent applications incorporated herein by reference.

Referring now to FIG. 1, a screenshot 100 of a start-up user interface screen of the Happify training software is shown. As shown in FIG. 1, the Happify training software provides two main functionalities. The first functionality, as outlined by a dotted box 101, is an option for training the natural language classifiers of the Happify system. As will be further described herein, selecting the first functionality 101 allows an administrative user to access the Happify database, retrieve and replay all of the Happify user responses stored in Happify database and review, with respect to each stored user response, results (i.e., classifications) of the various natural language classifiers employed by the Happify system. This functionality of the Happify training software will be further described herein with reference to FIGS. 1-4. The second functionality, as outlined by a dotted box 102, is an option for reviewing dialogues stored in the Happify database. As will be further described herein, selecting the second functionality 102 allows the administrative user to access the Happify database, to retrieve and replay each and every dialogue between the Happify system and a Happify user, to review each system generated prompts during the interaction for quality, and to modify a flow of the interaction as necessary for improvement. This feature of the Happify training software will be further described herein with reference to FIGS. 5-7.

As further shown in the screenshot 100 of FIG. 1, the start-up user interface screen of the Happify training software provides an option for narrowing down search results (e.g., outlined by a dotted box 103). Here, the administrative user can set the number of user responses to review at once and the order in which the queried user responses will appear. As also shown in the screenshot 100 of FIG. 1, the administrative user can initiate the review process under the first functionality 101 by using a start button (e.g., outlined by a dotted box 104). It is noted that the layout and the components of the start-up user interface screen 100 of the Happify training software as specifically illustrated in FIG. 1 are merely exemplary and are not intended to be limiting. Other information relevant to reviewing/training classifiers and dialogues can be included without departing from the scope of the present invention. The visual display of the Happify training software may be adapted to accommodate different versions or embodiments of the Happify system. It is also noted that numerous inventive aspects of the present invention lies not within a specific layout or a particular arrangement of icons/buttons, but in the features and functionalities enabled by the Happify training software in effectuating modifications and improvements to the Happify service providing computing systems.

Figure 2:
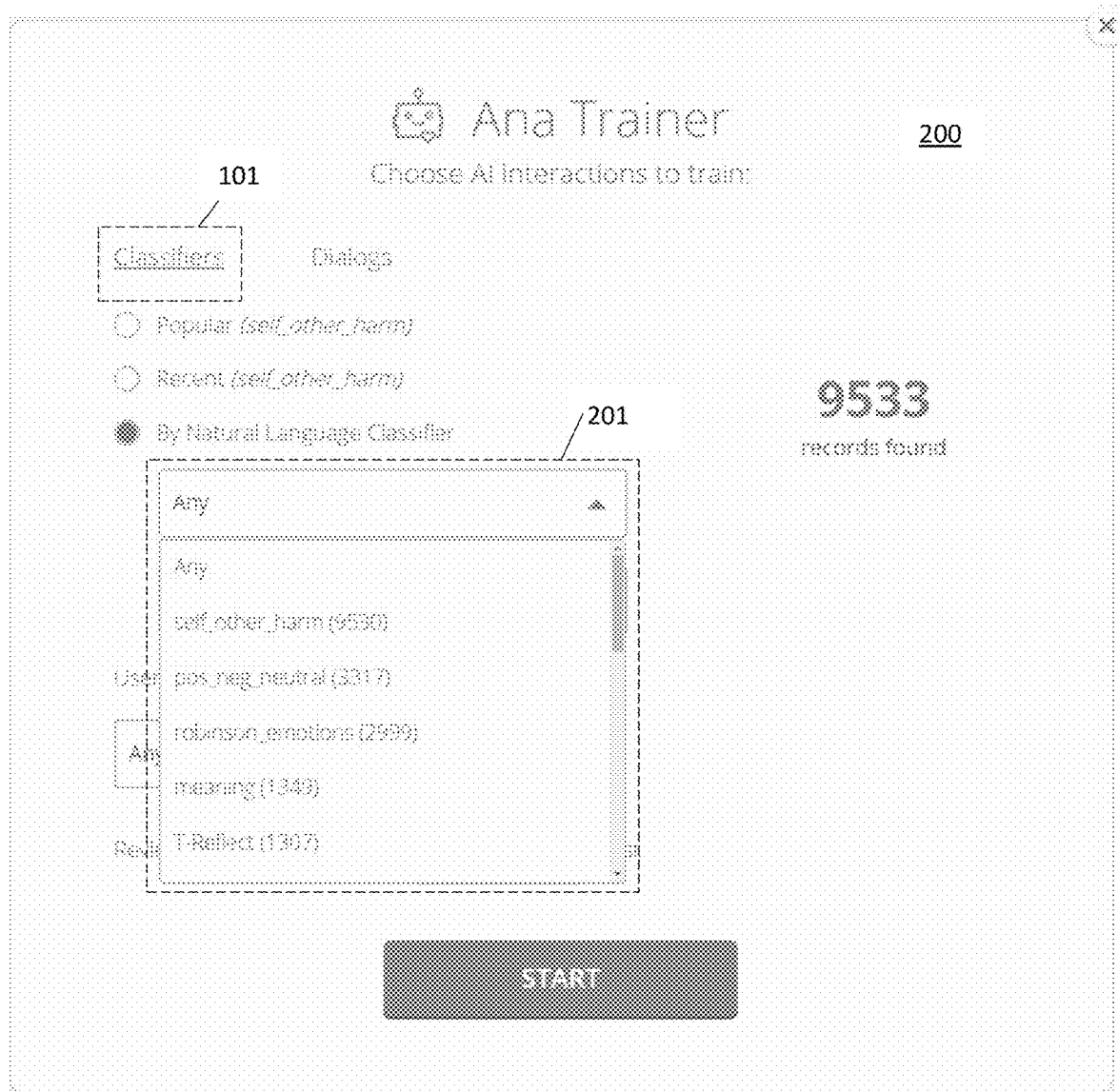
FIG. 2 is another screenshot of the start-up user-interface screen in accordance with the present invention.

Referring now to FIG. 2, a screenshot 200 of the start-up user interface screen of the Happify training software is shown. Under the first functionality 101 for reviewing the natural language classifiers, the training software provides a first drop-down menu 201 in which the administrative user can select from a plurality of natural language classifiers. As described herein, the Happify system is designed to employ a number of natural language classifiers in analyzing user responses. For example, one natural language classifier is a classifier designed to "classify" a user response as having a positive content, a negative content or a neutral content (i.e., the "pos_neg_neutral classifier"). As shown in FIG. 2, the Happify system, for example, has stored in its database thousands of user responses in which the pos_neg_neutral classifier has been invoked to classify user responses as containing either "positive," "negative," or "neutral" subject matter. Other exemplary natural language classifiers used by the Happify system are "T-Reflect" classifier, which is a classifier designed to be invoked when the Happify system detects user responses related to a "Thankfulness-Reflection" exercise of a Happiness track, the "T-Reflect" classifier particularly being designed to detect topics ranging from "good morning," "coffee," "overcoming adversity," "important people in your life," etc., and "self_other_harm" classifier, which is a classifier designed to detect from a user response subject matter belonging to either a class of neutral or no risk to selr or others and a class of potentially harmful to self or others. The natural language classifiers as shown and described herein are not intended to limit the scope of the present invention. Other natural language classifiers not shown and described herein may be utilized by the Happify system without departing from the scope and spirit of the present invention.

As the number of natural language classifiers used by the Happify system grows, and the number of user responses (e.g., training data) stored in the database grows to the hundreds of thousands, it becomes necessary to provide the administrative user an option to conduct a more specific and directed review. The first drop-down menu 201 permits the administrative user to select one natural language classifier to review at once, while also providing an option to review all training data at once.

Figure 3:
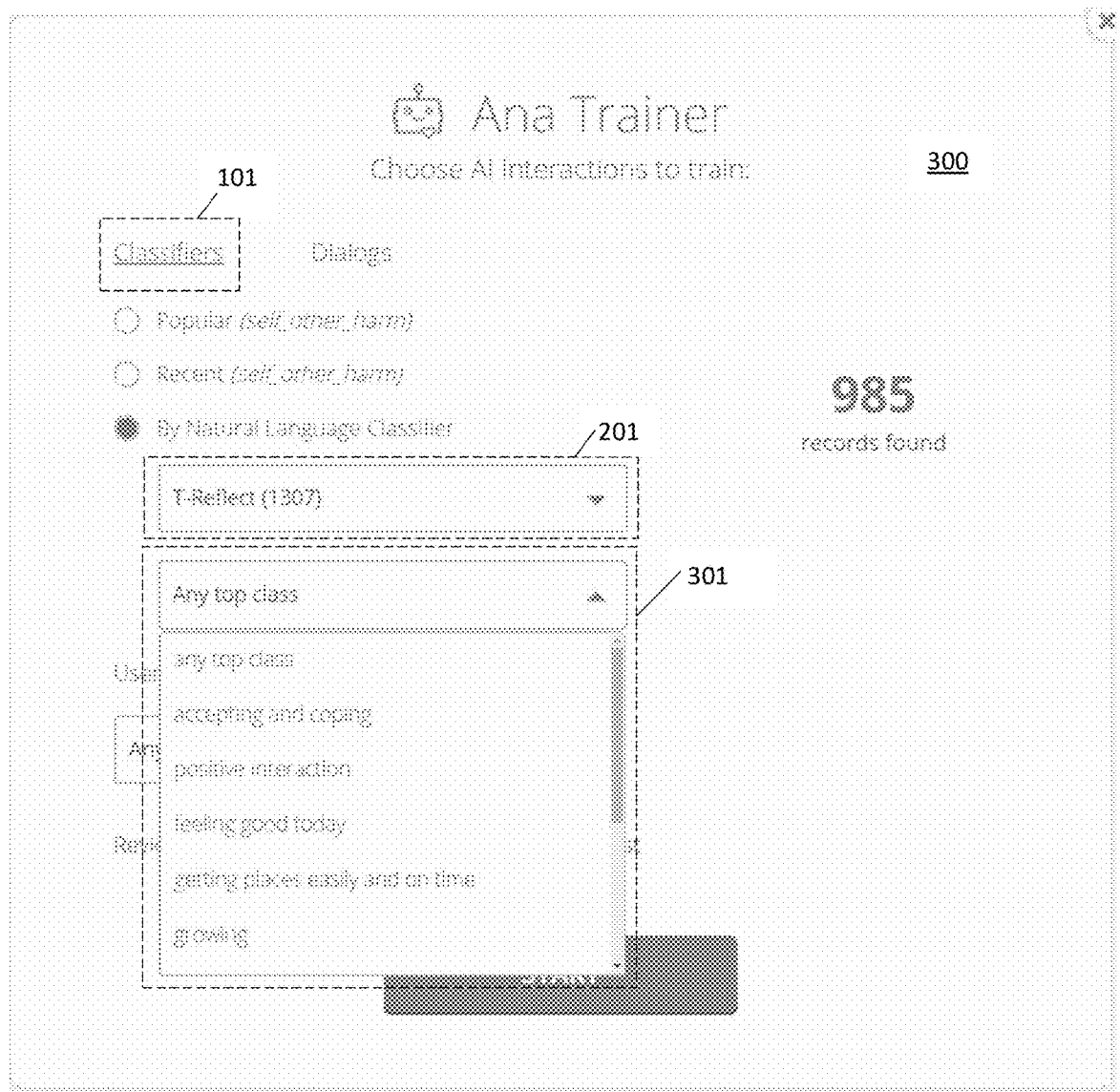
FIG. 3 is another screenshot of the start-up user-interface screen in accordance with the present invention.

FIG. 3 shows yet another screenshot 300 of the start-up user interface screen of the Happify training software that provides an additional narrowing option. Under the first functionality 101, once the administrative user selects a natural language classifier to review (e.g., via the first drop-down menu 201), the Happify training software also provides a second drop-down menu 301. With the second drop-down menu 301, the administrative user can further narrow the list of reviewable user responses under the selected classifier to only those user responses having a specific "top class" label. The second drop-down menu 301 can significantly reduce the number of user responses that may be returned for a query and allow the administrative user to perform a more efficient and thorough review of a natural language classifier in action. Additional details regarding the feature of a natural language classifier of the Happify system designating a "top class" to a user response is disclosed in U.S. patent application Ser. No. 15/974,978, the entire content of which is incorporated herein by reference.

Figure 4A:
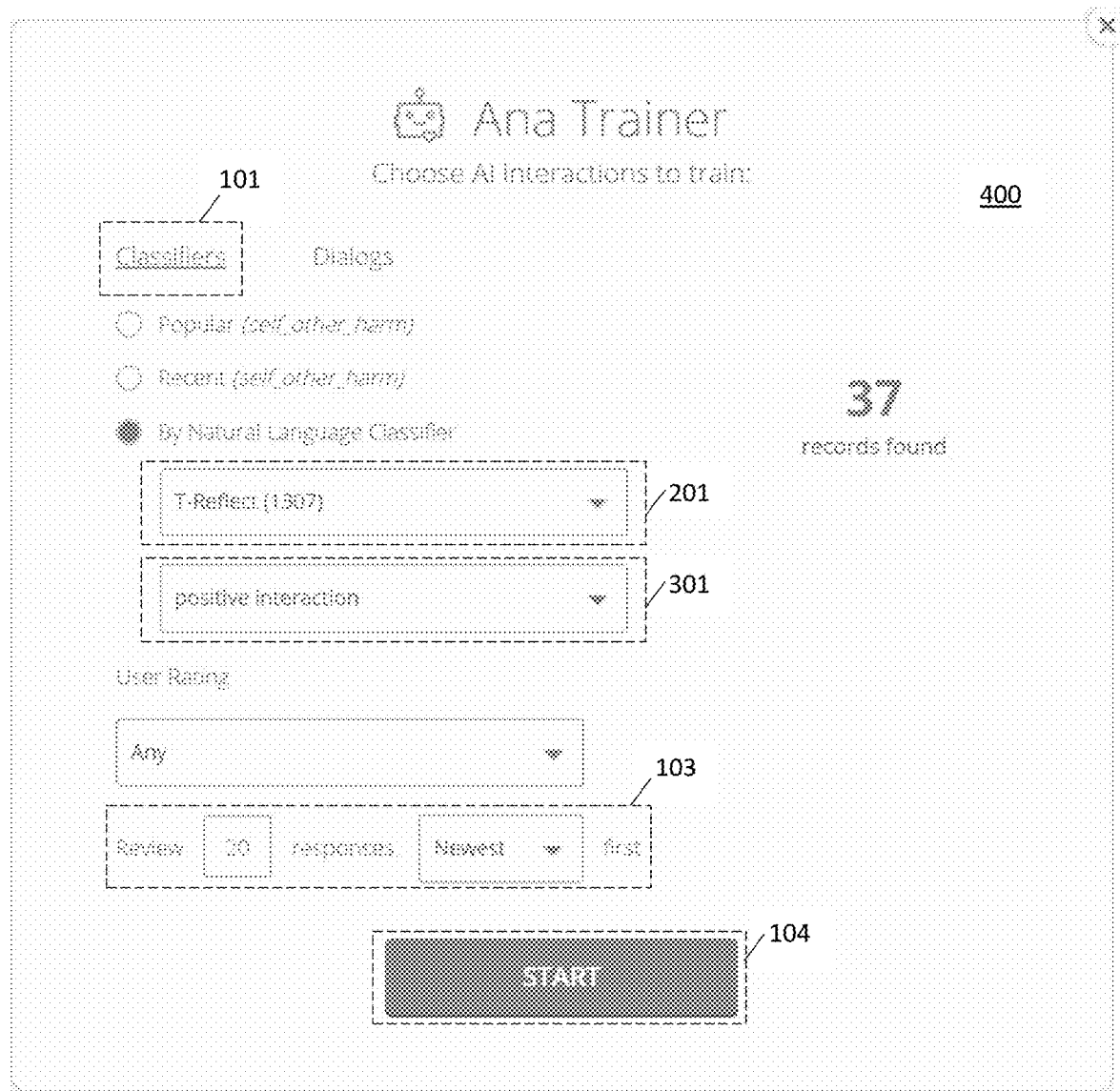
FIGS. 4A-4F are screenshots illustrating a training process in accordance with a first functionality of the present invention.

Returning back to the drawings, an example of training a natural language classifier will now be described with reference to FIGS. 4A-4F. FIG. 4A is a screenshot 400 of a start-up user interface screen of the Happify training software, similar to the screenshots shown with reference to FIGS. 1-3. In this particular example, the administrative user has selected to review the "T-Reflect" natural language classifier and, particularly, the user responses in which "positive interaction" was returned as the top class. The training process begins using the start button 104.

Figure 4B:
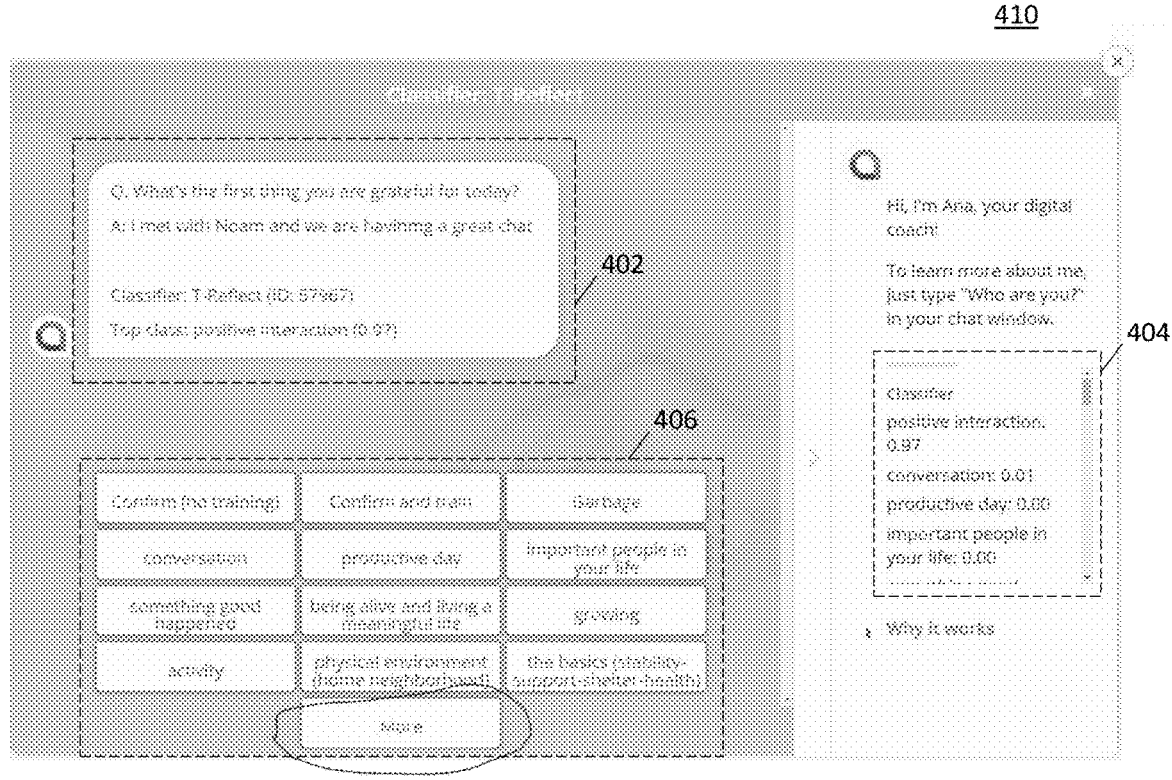

As shown in FIG. 4B, the Happify training software transitions from the start-up user interface screen 400 to a training screen 410. The training screen 410 is mainly comprised of three sections. The first section is referred to herein as the "dialogue display" section 402. In accordance with the display setting rules set by the administrative user (e.g., using the first and second drop-down menus and the box 103), the Happify training software displays in the dialogue display section 402 of the training screen 410 one user response for review at a time. The second section is referred to herein as the "top class results" section 404. The top class results section 404 of the training screen 410 displays every class returned for a user response along with a respective confidence score. Additional details regarding the feature of the natural language classifier returning top classes and assigning respective confidence scores are disclosed in U.S. patent application Ser. No. 15/974,978, the entire content of which is incorporated herein by reference.

The top class results section 404 generally orders the classes by the confidence scores (e.g., from high to low), and in most cases, the top class as chosen by the administrative user for review at the start-up user interface screen 400 appears at the top of the list. Finally, the third section is referred to herein as the "label-and-train" section 406. The label-and-train section 406 of the training screen 410 provides two sub-functionalities. First, the administrative user can confirm validity of a top class that has been returned for a particular user response. Second, if a top class returned for a particular user response appears to be incorrect, the administrative user can indicate another class as the correct top class by selecting a different class and training the classifier with the indication.

Returning back to the example, FIG. 4B shows that the particular user response displayed in the dialogue display section 402 is from an activity that is designed to increase the user's thankfulness skill. As part of the activity, a Happify user was asked to note things that the user is grateful for and the user responded with the statement, "I met with Noam and we are having a great chat." The T-Reflect classifier of the Happify system has classified that this particular user response belongs to the topic of "positive interaction" with a confidence score of "0.97" (1 being the highest).

One of the main purposes of the Happify training software is to enable a system administrator to review whether this decision by the classifier was a correct one, and if the decision was not a correct one, then enabling the system administrator to correct the decision and to add the correction as additional training data. For instance, in this example, the user response "I met with Noam and we are having a great chat" does appear to belong to the topic of "positive interaction," and it was indeed correct for the T-Reflect classifier to return "positive interaction" as the top class with a high confidence score of 0.97. The terms such as "having a great chat" also correspond highly to the confidence score of 0.97. As a result, the administrative user can visually confirm that the decision by the classifier was a correct one, select "Confirm (no training)," and move onto the next user dialogue (FIG. 4D).

Figure 4C:
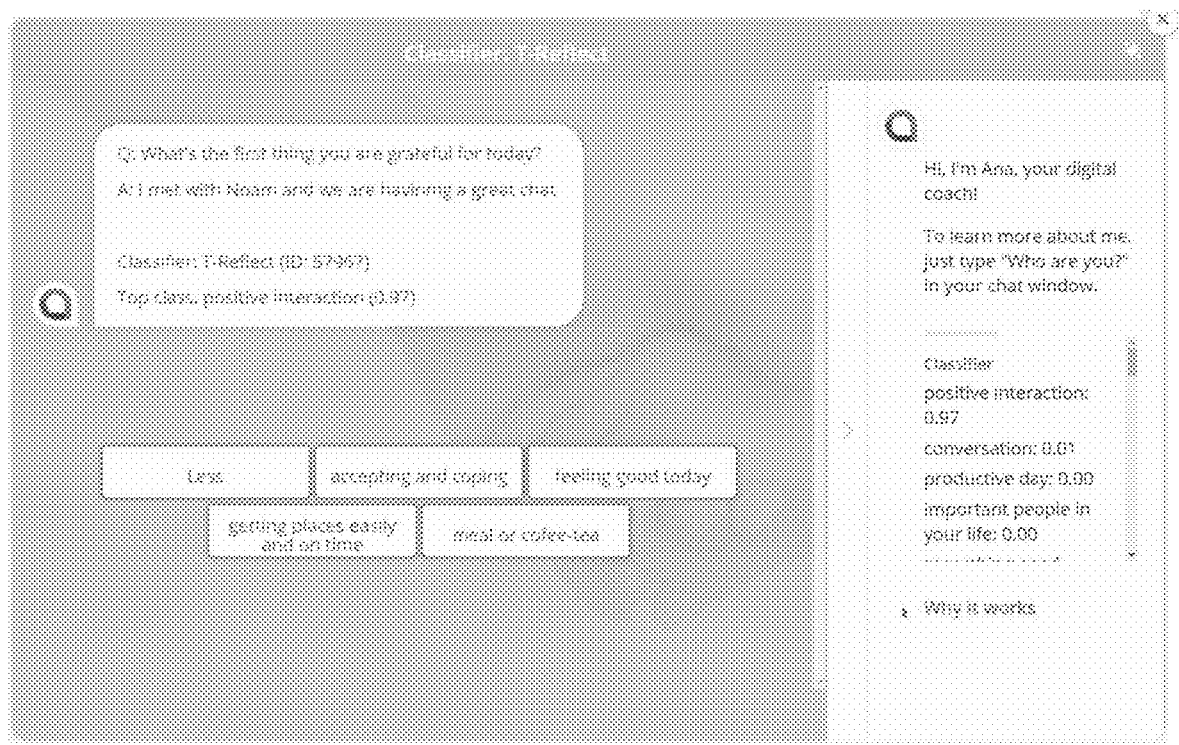
Figure 4D:
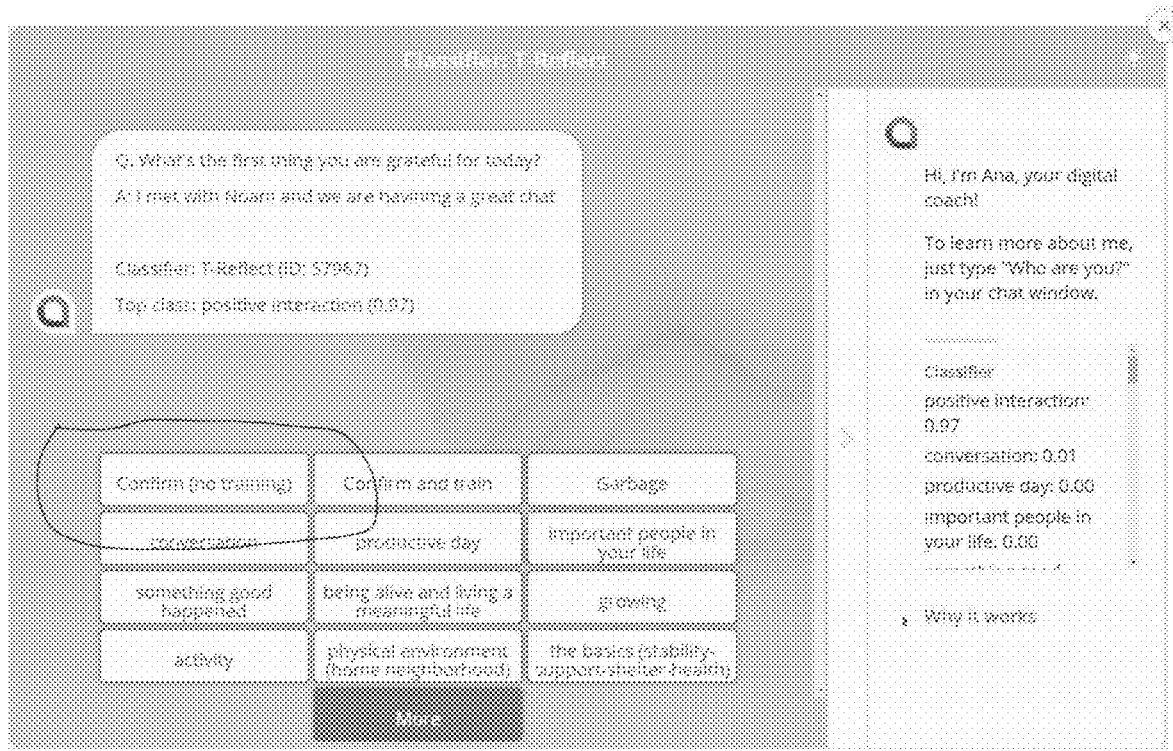

If, on the other hand, the administrative user finds that the context of the user response for review appears to belong in a class other than "positive interaction," the administrative user can correct this discrepancy by selecting a correct class from among the choices of classes available in the label-and-train section 406 (or from the expanded choices as shown in FIG. 4C). Once the correct class has been chosen, the administrative user can select "Confirm and train" and add the updated information to the training database.

In accordance with the present invention, each natural language classifier is associated with a respective spreadsheet of training data. Each spreadsheet of training data has stored therein details of every dialogue invoking the respective classifier. More specifically, the spreadsheet comprises columns and rows of data indicated by indicators such as user ids, dialogue ids, system prompt ids, user response ids, etc. listing every Happify user interaction that invoked the respective classifier. In accordance with the example above, the "T-Reflect" natural language classifier similarly has a training data spreadsheet of its own, and when the administrative user has created new training data by correcting an action of a classifier (i.e., selecting "Confirm and train"), a new line of data gets added to the training data spreadsheet (when the administrative user selects "confirm (no training)," no new line is added to the spreadsheet). The updated spreadsheet is then fed into an algorithm that re-trains from it the particular natural language classifier based on the added training data.

Figure 4E:
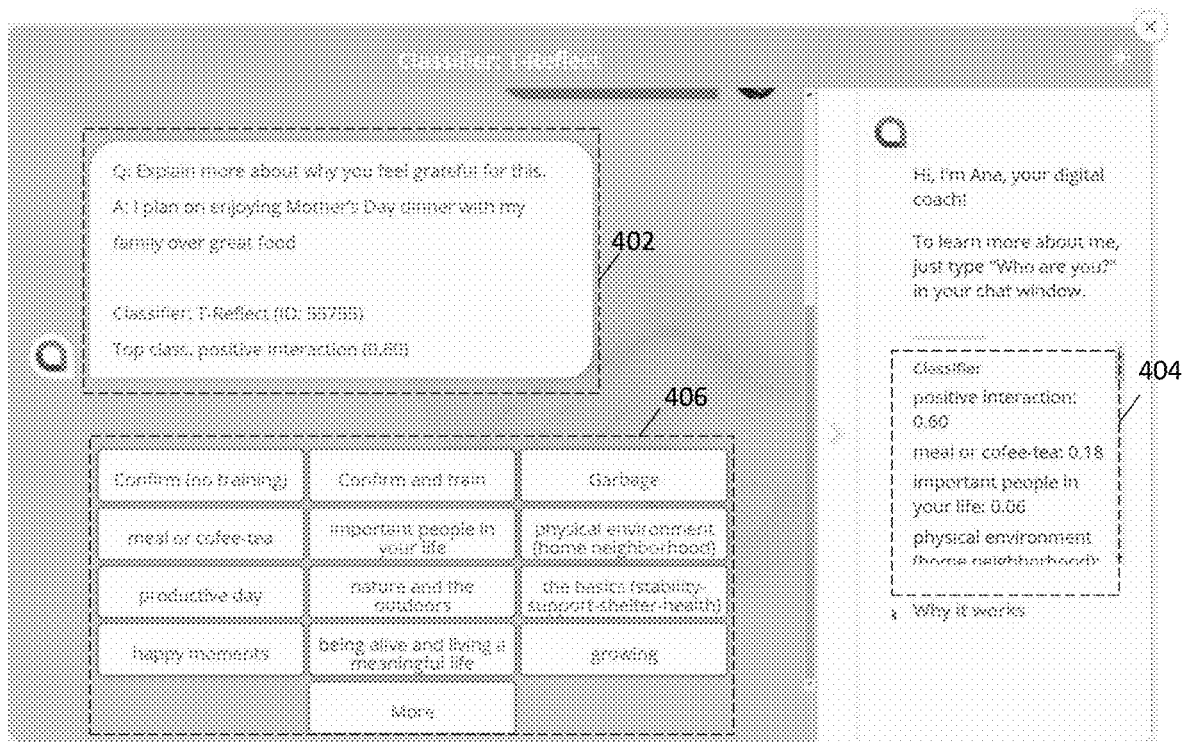
Figure 4F:
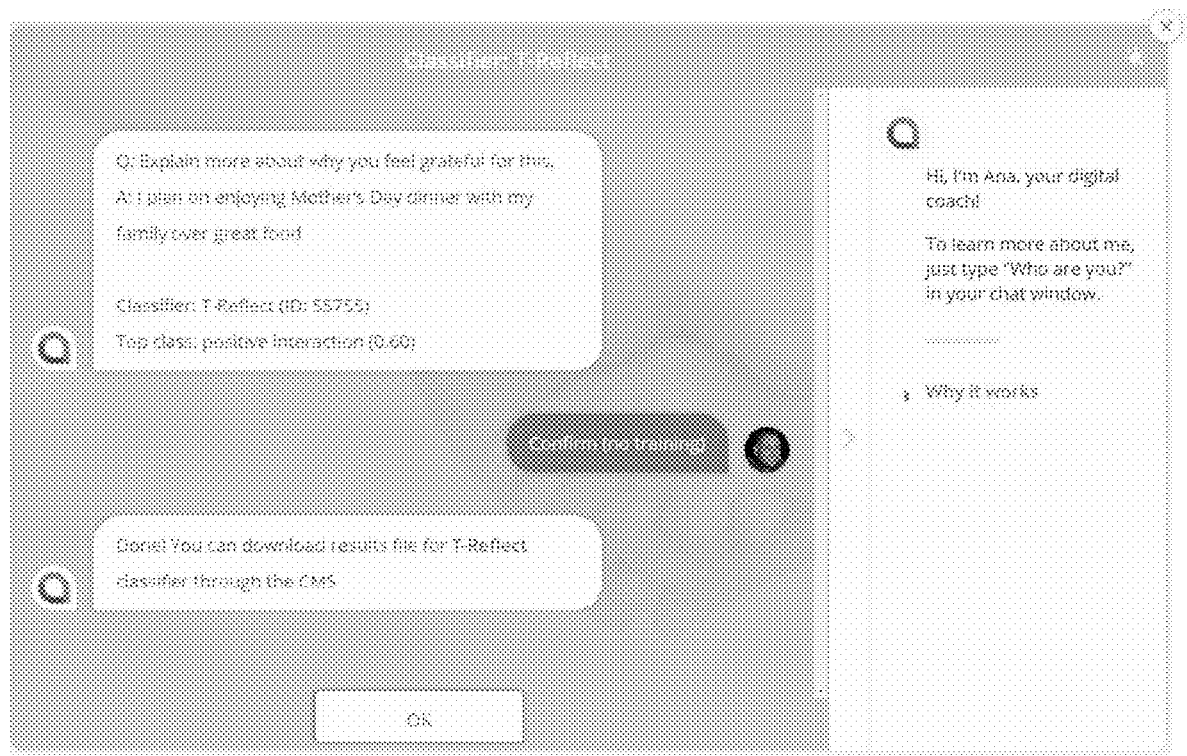

Returning back to FIGS. 4E-4F, the next user response is displayed in the dialogue display section 402. As shown in FIG. 4E, a Happify user was asked to elaborate on why the user feels grateful and the user responded with the statement, "I plan on enjoying Mother's Day dinner with my family over great food." As also shown in FIG. 4E, the T-Reflect classifier has classified that this user response also belongs to the topic of "positive interaction," with a confidence score of "0.60." Similar to the previous user response, this user response "I plan on enjoying Mother's Day dinner with my family over great food" also does appear to belong to the topic of "positive interaction" as indicated by terms such as "enjoying" and "great food." Hence, the administrative user can visually confirm the validity of the classifier with respect to this user response. The administrative user may also, however, note that the confidence score is relatively lower than the previous user response, as there are terms in the user's response that may also appropriately belong to other classes (e.g., "Mother's Day" and "family" may belong to the class "important people in your life" or "dinner" and "great food" may belong to the class "meal or coffee-tea"). As with the previous user response, the Happify training software enables the administrative user, upon reviewing the results of the classifier, to confirm and conclude that no further training is necessary with respect to this particular user response. The process then continues to the next user response.

The examples described with reference to FIGS. 4A-4F are only exemplary illustrations of the Happify training software's first functionality. As illustrated via these examples, the Happify training software provides an environment in which a person with administrative access can access the Happify database, replay (and visually review) each and every dialogue between a Happify user and the Happify system and assess how well (or how accurately) the natural language classifiers of the Happify system have analyzed user input data. More particularly, the Happify training software displays pertinent information on a user-interface display screen and allows the administrator to perform a more directed and efficient review of user responses to create additional training data that can in turn be used to re-train the respective natural language classifiers. As a result, the natural language classifiers of the Happify system are re-trained, and the accuracy and efficiency of the Happify system with respect to future user interactions is optimized.

The second functionality of the Happify training software will now be described with reference to FIGS. 5-7. As described herein, the Happify training software enables the system administrator to access the Happify database, replay user dialogues, review system generated prompts during the interaction for quality, and modify the flow of the interaction as necessary.

Figure 5:
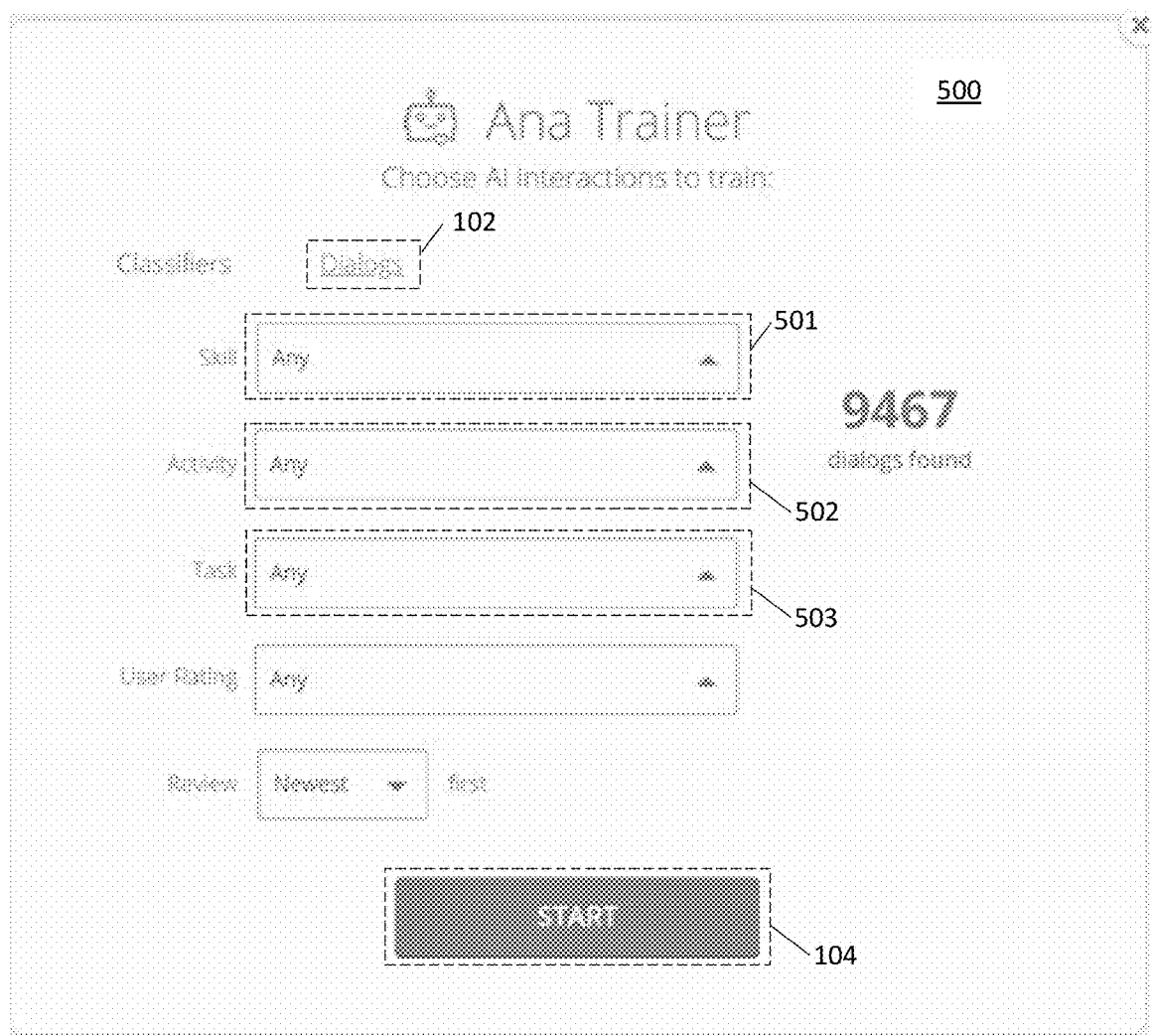
FIG. 5 is another screenshot of the start-up user-interface screen in accordance with the present invention.
Figure 6:
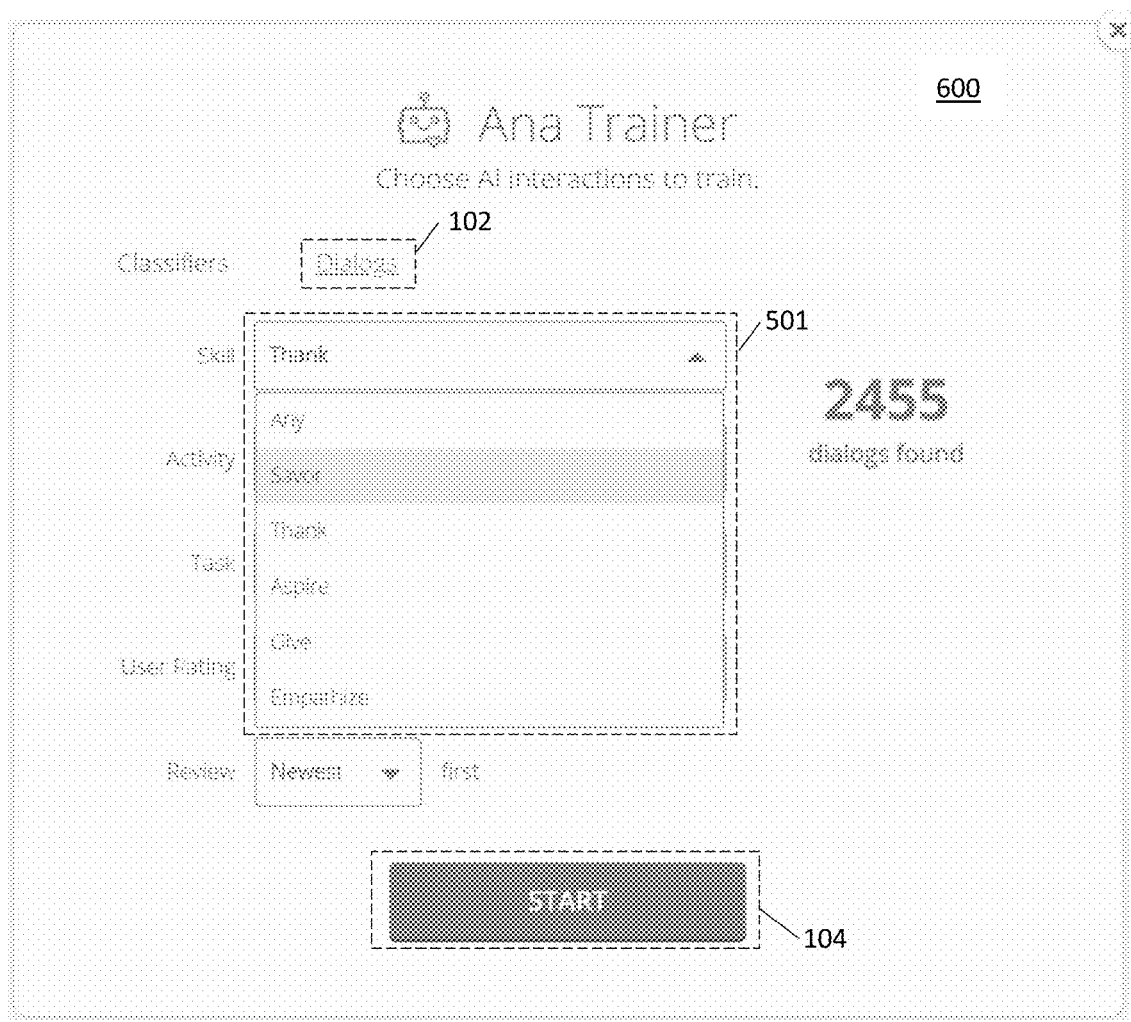
FIG. 6 is another screenshot of the start-up user-interface screen in accordance with the present invention.

Referring now to FIG. 5, a screenshot 500 of a start-up user interface screen of the Happify training software is shown, similar to the screenshots described with reference to FIG. 1. As shown in FIG. 5, the second functionality 102 is selected, and the start-up user interface screen shows a plurality of drop-down menus 501, 502 and 503. Similar to the first functionality, the Happify training software provides, for the second functionality, options for the system administrator to narrow down which dialogues to review first. Upon selection(s) via the drop-down menus 501, 502 and 503, the system administrator begins the review process by using the start box 104.

As previously described herein, every dialogue between each Happify user and the Happify system that ever takes place is stored in the Happify system database. In accordance with the present invention, the stored dialogues are categorized by skills (e.g., S.T.A.G.E.™), activities and/or tasks. This particular grouping of the dialogues allows for a more focused and efficient review process. As shown in the screenshot 600 of FIG. 6, choosing from the drop-down menus 501, 502 and/or 503 efficiently reduces the number of dialogues that will be presented for review at once.

Figure 7A:
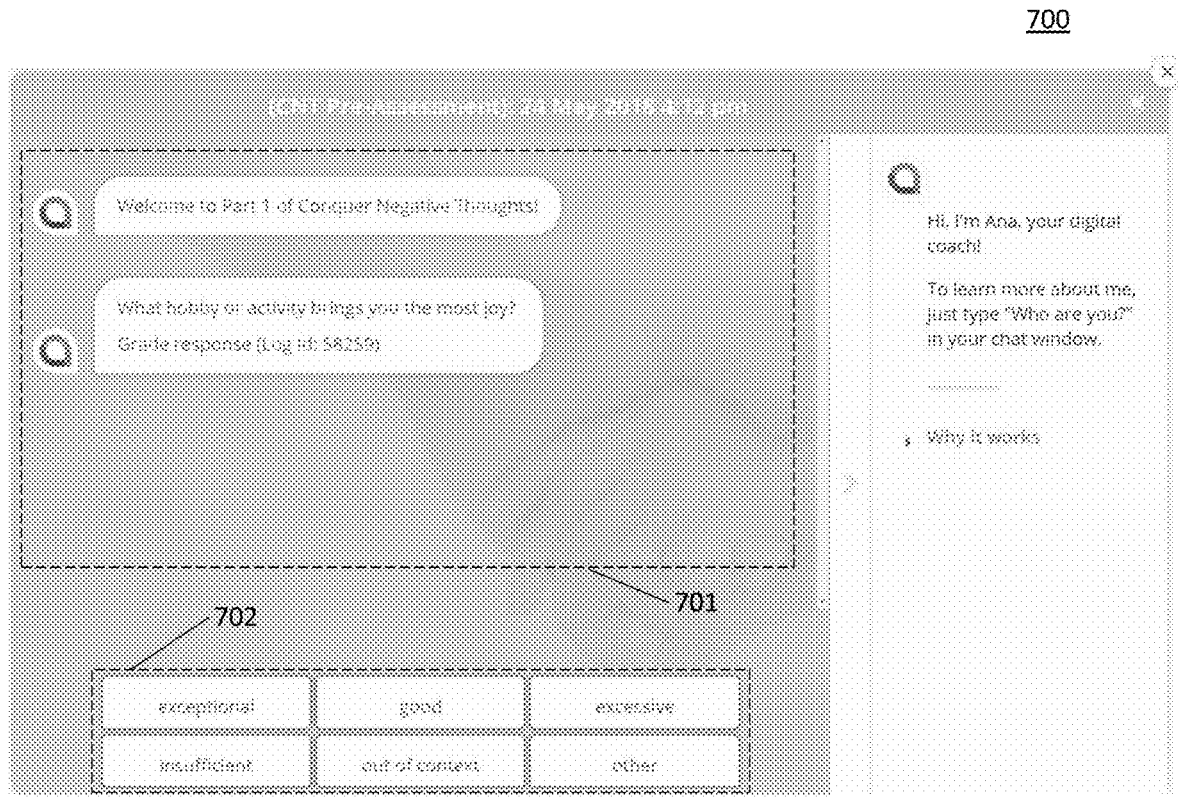
FIGS. 7A-7F are screenshots illustrating another training process in accordance with a second functionality of the present invention.

An example of reviewing dialogues and altering a flow an interaction will now be described with reference to FIGS. 7A-7F. FIG. 7A shows a training screen 700 which is mainly comprised of two sections. The first section is referred to herein as the "dialogue display" section 701. The dialogue display section 701 first displays a computer generated prompt, followed by a user response. The second section is referred to herein as the "rate-and-comment" section 702. The rate-and-comment section 702 provides the administrative user with a plurality of degrees of rating options for rating the quality of each of the computer generated prompt. In accordance with the present invention, the rating of the computer generated prompt is for the purpose of determining whether the computer generated prompt is appropriate, supportive and emotionally intelligent as being in line with the underlying concept of the Happify service system. The plurality of degrees of rating options are, for example, "exceptional," "good," "excessive," "insufficient," "out of context," etc. These examples are not intended to be limiting and other degrees of ratings may be used herein without departing from the scope of the present invention. As such, these terms can be substituted by appropriate other terms having the same or similar meaning and, thus, usage of these terms is intended to also encompass synonymous terms and/or terms with sufficiently similar meanings. If there is no appropriate degree of rating option, the administrative user can select "other" and provide a different rating. Whenever a prompt is rated, the Happify training software may require the administrative user to provide reasons behind the particular rating.

Figure 7B:
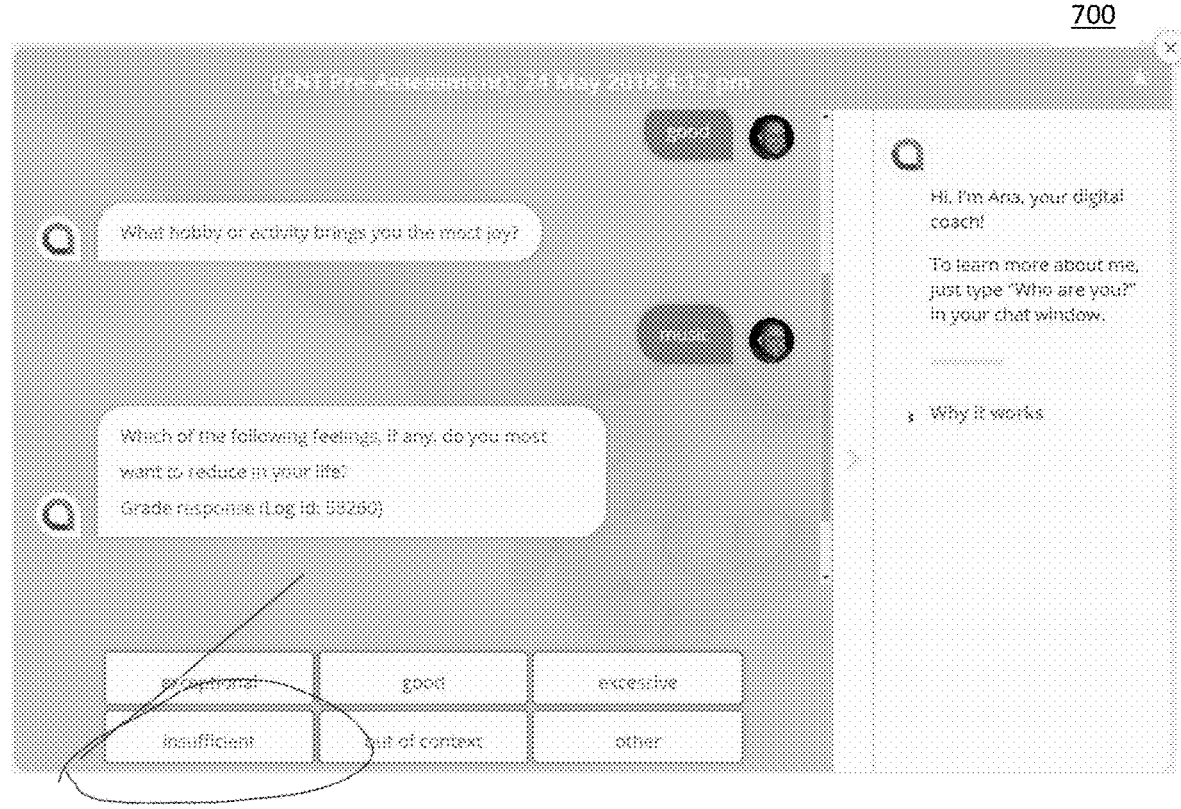

Returning back to the example, and particularly to FIGS. 7A-7B, a first prompt to be reviewed is "What hobby or activity brings you the most joy?" Since this first prompt is merely a question to start the dialogue, there is not much context for the administrative user to review on whether the prompt is emotionally intelligent or not. This is mainly because the initial prompt is not formulated in response to a user response. In such case, the administrative user may simply select the rating "good" (or a rating of similar nature) and move onto the next prompt.

Figure 7C:
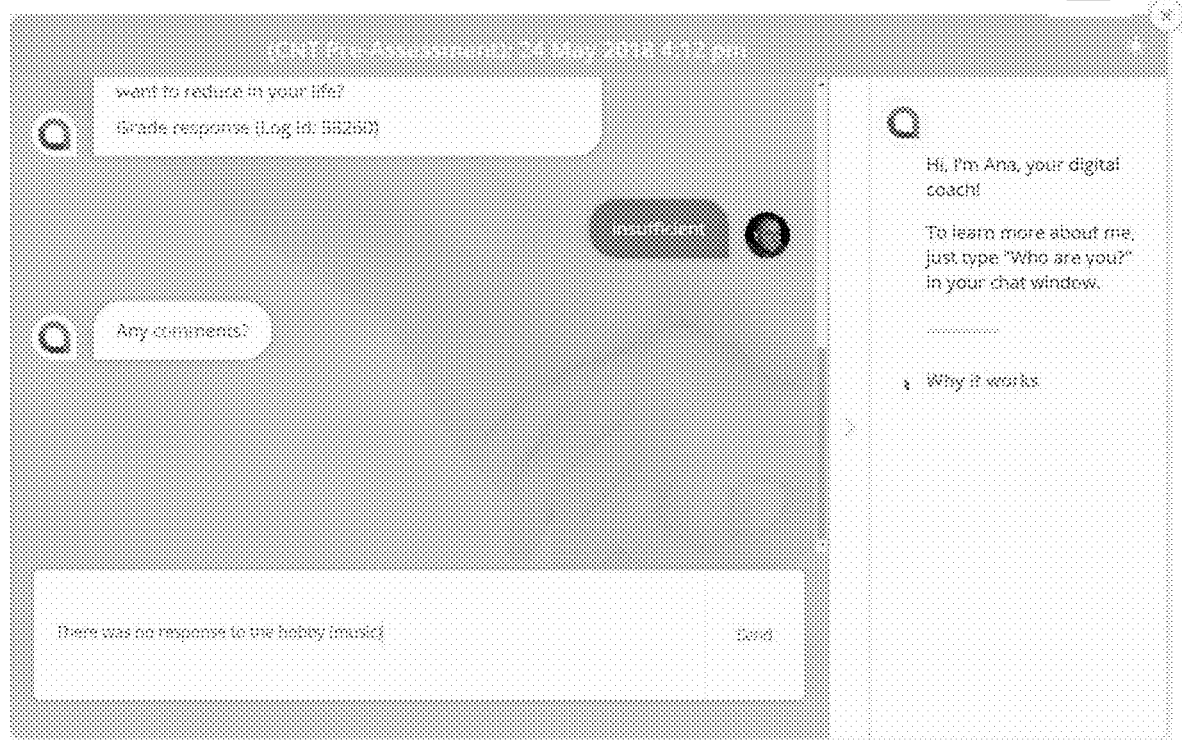

As shown in FIG. 7B, in response to the first prompt, a Happify user has answered "music." Next, in response to the user response "music," a second computer generated prompt is provided, which reads "Which of the following feelings, if any, do you most want to reduce in your life?" This time, unlike the first prompt, the administrative user has enough context to review whether the second prompt was an emotionally intelligent one. In this example, although the Happify user responded with "music," nothing in the second prompt is reflective of the user's response. Here, the quality of the computer generated prompt is evaluated based on whether the prompt is mirroring the user's response. As such, since the administrative user can clearly see that the second computer generated prompt is not mirroring the context of the user's response, the administrative user may select the rating "insufficient" (or a rating of similar nature) and provide a comment as to why such prompt is labeled as "insufficient" (FIG. 7C). In accordance with the present invention, the evaluation of the computer generated prompt on the scale of its mirroring ability is only an example, and other standards for evaluating the computer generated prompt may be employed without departing from the scope of the present invention.

As illustrated via the example from FIGS. 7A-7C, the purpose of the second functionality of the Happify training software is for the administrative user to replay a Happify dialogue, review the content of each computer generated prompt, and make an indication of whether each of the computer generated prompts was an emotionally intelligent prompt. The indications as made by the administrative user are saved and may be generated as a report, which then may be used by software engineers/developers (e.g., Happify interaction designers) to ensure in future Happify user interactions, a similar conversation receiving a similar user response would take a different turn (i.e., with a more emotionally intelligent prompt), thereby altering the flow of the interaction.

Figure 7D:
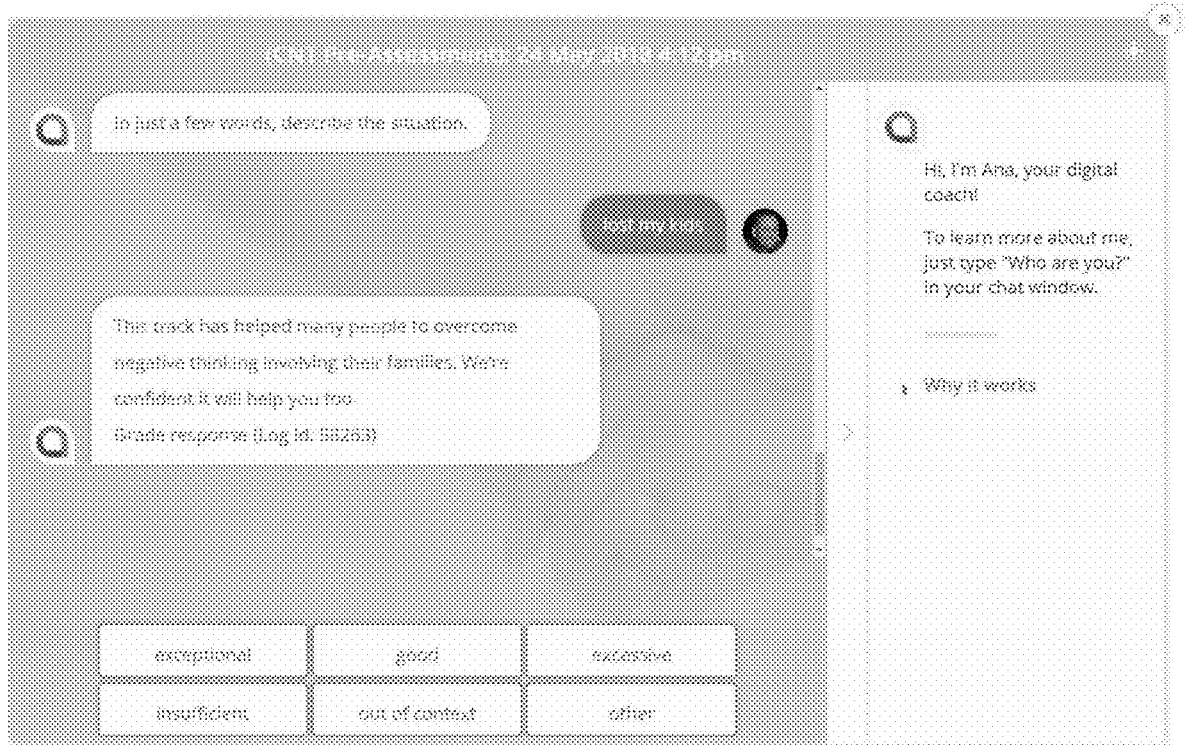
Figure 7E:
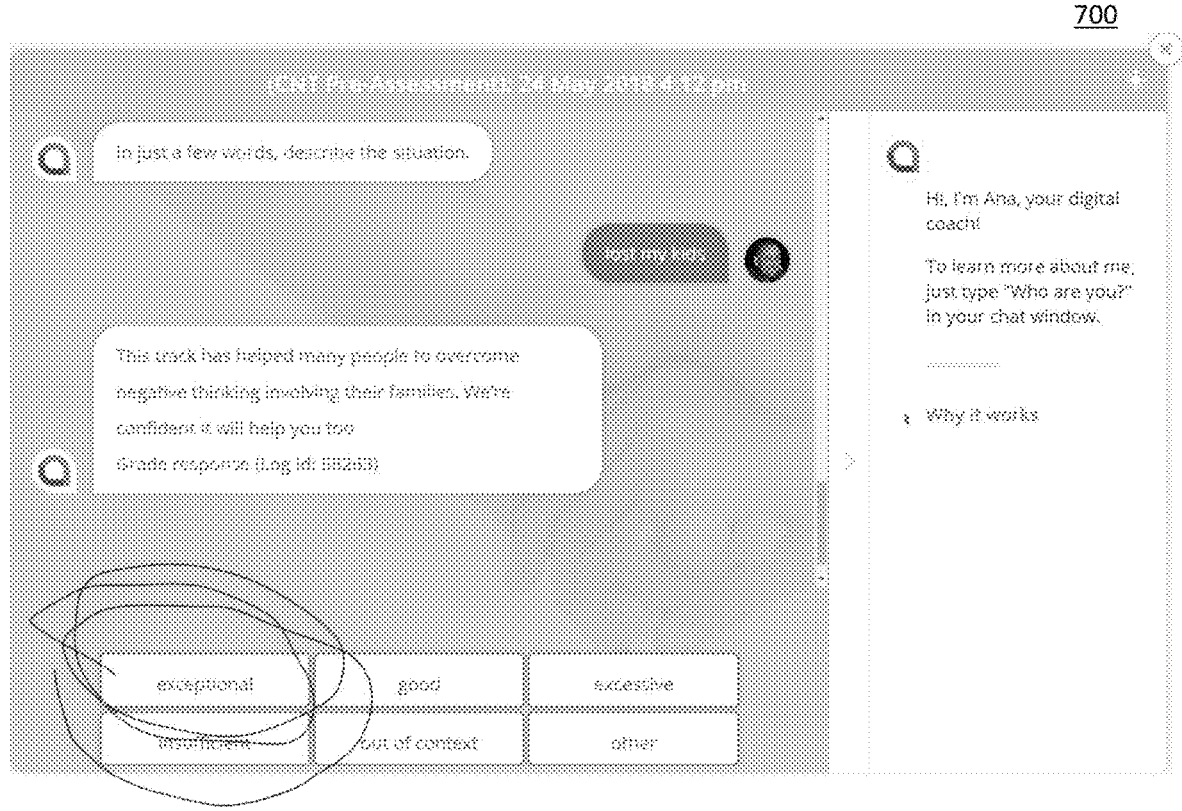
Figure 7F:
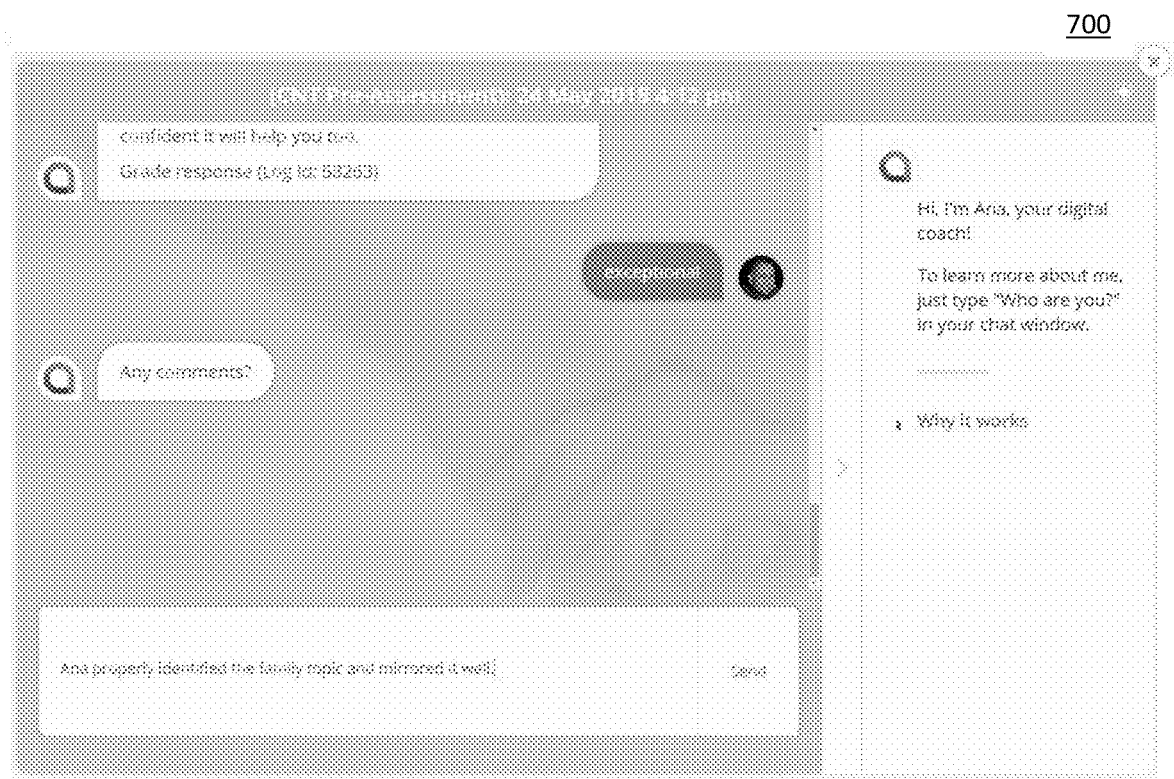

Returning back to the drawings, FIG. 7D shows a third prompt in which the Happify system has asked a Happify user to describe a situation. The Happify user has responded with "lost my kids." In response, the Happify system responded with a follow up computer generated prompt that reads, "This track has helped many people to overcome negative thinking involving their families. We're confident it will help you too." The administrative user assesses, under the context of "lost my kids," the computer generated prompt and evaluates that the prompt was in fact "emotionally intelligent" as it properly identified the topic "family" and mirrored it well in its prompt. As shown in FIGS. 7E-7F, the administrative user may in such case select the rating "exceptional" (or a rating of similar nature) and provide a comment as to why such prompt is labeled as "exceptional."

Similar to the example dialogue as shown with FIGS. 7A-7C, the administrative user in FIGS. 7D-7F has replayed a dialogue, evaluated into a computer generated prompt, and made an indication as to whether the computer generated prompt was an emotionally intelligent prompt. Similarly, this indication made by the administrative user is saved and may be generated as a report that would ensure future Happify user interactions to reflect this particular indication.

The examples described with reference to FIGS. 7A-7F are only exemplary illustration of the Happify training software's second functionality. As illustrated from the foregoing, the administrative user is evaluating the quality of the prompts. For instance, as already discussed herein, the prompts are being evaluated based on how well they mirror the prior user response. In another instance, the prompts are being evaluated based on how well they support the flow of the dialogue. More particularly, a prompt should be conducive of the prompts that follow, and the resulting flow of the dialogue should seem natural. Any prompt that makes a dialogue seem as if a Happify user is "talking to a machine with no capability of understanding and responding appropriately" should be flagged. Moreover, any prompts (or comments) that are out-of-context or that seem to steer the dialogue in a way that does not make sense should also be flagged. In yet another instance, the prompts are being evaluated based on how well they maximize a Happify user's adherence fidelity. In other words, the prompts should steer the user toward the best possible adherence. If they do not, the prompts should be flagged so that they can be improved.

As illustrated via these examples, each of the prompts generated by the Happify system can be evaluated/rated based on its respective quality. As already discussed herein, the manner in which the administrative user can make an evaluation includes, for example, but not limited to, being provided with a plurality of selectable ratings and selecting one or more of the most appropriate ratings. The labels, or various degrees of ratings, as disclosed herein such as "exceptional," "good," "excessive," "insufficient," "out of context," etc. are exemplary and a part of a non-exhaustive list. Other appropriate terms may be applied interchangeably as deemed necessary to provide a more dynamic range of evaluation.

In accordance with the second functionality of the Happify training software, system generated prompts provided during the Happify interactions can be reviewed for quality. Ideally, in accordance with the underlying principle of the Happify service, every prompt provided by the Happify system should be artificially intelligent in its respective context. The Happify training software provides an environment in which useful and accurate human evaluations can be made, which in turn may positively improve flows of dialogues in Happify user interactions.

Similar to the natural language classifier training sessions as described herein with reference to FIGS. 1-4, in some embodiments, the result of reviewing the dialogues under the second functionality of the Happify training software is also a spreadsheet that includes a log of the turns in the dialogues and how the administrative user has rated each prompt and/or turn. The spreadsheet as generated by the Happify training software may be in a downloadable/printable form and may be exported for various other purposes.

In accordance with the present disclosure, appearances of the phrase "in an embodiment" or "in an exemplary embodiment," or any other variations of this phrase, appearing in various places throughout the specification are not necessarily all referring to the same embodiment, and only mean that a particular characteristic, feature, structure, and so forth described in connection with the embodiment described is included in at least one embodiment.

The technology described herein may be incorporated in a system, a method, and/or a computer program product, the product including a non-transitory computer readable storage medium having program instructions that are readable by a computer, causing aspects of one or more embodiments to be carried out by a processor. The program instructions are readable by a computer and can be downloaded to a computing/processing device or devices from a computer readable storage medium or to an external computer or external storage device via a network, which can comprise a local or wide area network, a wireless network, or the Internet.

Additionally, the network may comprise wireless transmission, routers, firewalls, switches, copper transmission cables, optical transmission fibers, edge servers, and/or gateway computers. Within the respective computing/processing device, a network adapter card or network interface in each computing/processing device receives computer readable program instructions from the network and forwards the computer readable program instructions for storage in a computer readable storage medium.

As used herein, a computer readable storage medium is not to be construed as being transitory signals, such as radio waves or other freely propagating electromagnetic waves, electromagnetic waves propagating through a waveguide or other transmission media, or electrical signals transmitted through a wire. The computer readable storage medium may be, but is not limited to, e.g., a magnetic storage device, an electronic storage device, an optical storage device, a semiconductor storage device, an electromagnetic storage device, or any suitable combination of the foregoing, and can be a tangible device that can retain and store instructions for use by an instruction execution device. The following is a list of more specific examples of the computer readable storage medium, but is not exhaustive: punch-cards, raised structures in a groove, or other mechanically encoded device having instructions recorded thereon, an erasable programmable read-only memory, a static random access memory, a portable compact disc read-only memory, a digital versatile disk, a portable computer diskette, a hard disk, a random access memory, a read-only memory, flash memory, a memory stick, a floppy disk, and any suitable combination of the foregoing.

The operations of one or more embodiments described herein may be carried out by program instructions which may be machine instructions, machine dependent instructions, microcode, assembler instructions, instruction-set-architecture instructions, firmware instructions, state-setting data, or either source code or object code written in any combination of one or more programming languages, including an object oriented programming language such as, but not limited to, C++, and other conventional procedural programming languages.

The program instructions, as will be clear to those skilled in the art from the context of the description, may have the capability of being executed entirely on a computer of a user, may also be executed partly on the computer of the user, partly on a remote computer and partly on the computer of the user, entirely on the remote computer or server, or as a stand-alone software package. In the "entirely on the remote computer or server" scenario, the remote computer may be connected to the user's computer through any type of network, including a wide area network or a local area network, or the connection may be made to an external computer. In some embodiments, electronic circuitry including, e.g., field-programmable gate arrays, programmable logic circuitry, or programmable logic arrays may execute the program instructions by utilizing state information of the program instructions to personalize the electronic circuitry, in order to perform aspects of one or more of the embodiments described herein. These program instructions may be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. These program instructions may also be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer readable program instructions may also be loaded onto a computer, other programming apparatus, or other device to produce a computer implemented process, such that the instructions which execute on the computer, other programmable apparatus, or other device implement the functions/acts specified in the flowchart and/or block diagram block or blocks.

The block and/or other diagrams and/or flowchart illustrations in the Figures are illustrative of the functionality, architecture, and operation of possible implementations of systems, methods, and computer program products according to the present invention's various embodiments. In this regard, each block in the block and/or other diagrams and/or flowchart illustrations may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently or sometimes in reverse order, depending upon the functionality involved. It will also be noted that each block of the block and/or other diagram and/or flowchart illustration, and combinations of blocks in the block and/or other diagram and/or flowchart illustration, can be implemented by special purpose hardware-based systems that perform the specified functions or acts or carry out combinations of special purpose hardware and computer instructions.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set. To aid the Patent Office and any readers of any patent issued on this application in interpreting the claims appended hereto, applicant wish to note that applicant does not intend any of the appended claims or claim elements to invoke 35 U.S.C. § 112(f) unless the words "means for" or "step for" are explicitly used in the particular claim.

In view of the foregoing disclosure, an inventive training software executable on a computing system has been described. In accordance with the disclosure provided herein, the inventive training software provides an environment for reviewing dialogues between an interactive computing system and a user of that interactive computing system. The inventive training software enables a provider of the interactive computing system to assess and train various functionalities within interactive system. More particularly, the training software enables training of natural language classifiers and training of computer-generated prompts under various standards. The inventive training software optimizes the accuracy and efficiency of the interactive system and the flow of the system-and-user interactions. Finally, the inventive training software optimizes future system-and-user interactions by continuously augmenting training data and combining human-level diagnosis to an artificially intelligent computing system.

Having described preferred embodiments of a computing system/method for enabling a user to improve, via training, a system designed to increase the emotional and/or physical well-being of persons, or designed for other purposes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims.

What is claimed is:

1. A computing system, comprising:
a user-interface display screen;
at least one processor; and
at least one memory storing executable training software which, when executed by the at least one processor, causes the at least one processor to:
access a database of dialogues, the dialogues including a plurality of computer- generated prompts and user responses to the prompts, wherein the user responses are previously received from users and stored in the database;
retrieve, from the database, at least one user response having already labeled thereto an assigned class having a highest confidence score, the confidence score indicating a degree of confidence that a context of the at least one retrieved user response is of the assigned class;
display, on the user-interface display screen, one or more natural language classifiers in a first drop-down menu;
display, on the user-interface display screen, a plurality of classes in a second drop-down menu, wherein selecting one of the plurality of classes in the second drop-down menu reduces a number of user responses reviewable under the one or more natural language classifiers displayed in the first drop-down menu;
display a training screen on the user-interface display screen, the training screen comprising a dialogue display section, a label-and-train section, and a top class results section, the dialogue display section comprising at least a portion of the dialogues, and the top class results section comprising at least the assigned class along with a plurality of other classes, each of the plurality of other classes having a respective lower confidence score than the assigned class, wherein the other classes are displayed in a predetermined order according to their confidence scores; and
receive, from a user of the training software, an indication of validity of the assigned class of the at least one retrieved user response,
wherein each of the confidence scores is pre-determined by one of the one or more natural language classifiers employed to analyze the at least one user response.

2. The computing system of claim 1, wherein the indication of validity comprises at least one of:
(a) a confirmation that the assigned class is correct; and
(b) a selection of one of the plurality of other classes,
wherein, when indication of validity comprises the selection of the one of the plurality of classes, the executable software stored in the at least one memory is adapted to cause the at least one processor to update the assigned class of the at least one retrieved user response with the selected one of the plurality of other classes to generate an updated user response, and
wherein, the confirmation that the assigned class is correct includes one of:
confirmation and training request; or
confirmation and no training request.

3. The computing system of claim 2, wherein, when indication of validity comprises the selection of the one of the plurality of other classes or the confirmation and training request, the executable software stored in the at least one memory is further adapted to cause the at least one processor to store the updated user response as new data to the database.

4. The computing system of claim 3, wherein the database with the new data is configured to be used to re-train the natural language classifier.

5. The computing system of claim 1, wherein the at least one retrieved user response has pre-associated therewith the assigned class with the highest confidence score and the plurality of other classes with the respective lower confidence scores.

6. The computing system of claim 1, wherein the dialogues stored in the database are configured to be from a series of interactions between an interactive computing system and a user of the interactive computing system.

7. The computing system of claim 6, wherein the series of interactions are a set of activities designed to cause an increase in a level of happiness of the user of the interactive computing system.

8. A method comprising:
accessing a database of dialogues, the dialogues including a plurality of computer- generated prompts and user responses to the prompts, wherein the user responses are previously received from users and stored in the database;
retrieving, from the database, at least one user response having already labeled thereto an assigned class having a highest confidence score, the confidence score indicating a degree of confidence that a context of the at least one retrieved user response is of the assigned class;
displaying, on the user-interface display screen, one or more natural language classifiers in a first drop-down menu;
displaying, on a user-interface display screen, a plurality of classes in a second drop-down menu, wherein selecting one of the plurality of classes in the second drop-down menu reduces a number of user responses reviewable under the one or more natural language classifiers displayed in the first drop-down menu;
displaying a training screen on the user-interface display screen, the training screen comprising a dialogue display section, a label-and-train section, and a top class results section, the dialogue display section comprising at least a portion of the dialogues, and the top class results section comprising at least the assigned class along with a plurality of other classes in a second drop-down menu, each of the plurality of other classes having a respective lower confidence score,
wherein the other classes are displayed in a predetermined order according to their confidence scores; and
receiving an indication of validity of the assigned class of the at least one retrieved user response,
wherein each of the confidence scores is pre-determined by one of the one or more natural language classifiers employed to analyze the at least one user response.

9. The method of claim 8, wherein the indication of validity comprises at least one of:
(a) a confirmation that the assigned class is correct; and
(b) a selection of one of the plurality of other classes,
wherein, when indication of validity comprises the selection of the one of the plurality of classes, the method further comprises updating the assigned class of the at least one retrieved user response with the selected one of the plurality of other classes to generate an updated user response, and
wherein, the confirmation that the assigned class is correct includes one of:
confirmation and training request; or
confirmation and no training request.

10. The method claim 9, wherein, when indication of validity comprises the selection of the one of the plurality of other classes or the confirmation and training request, the method further comprises storing the updated user response as new data to the database.

11. The method claim 10, wherein the database with the new data is configured to be used to re-train the natural language classifier.

12. The method of claim 8, wherein the at least one retrieved user response has pre-associated therewith the assigned class with the highest confidence score and the plurality of other classes with the respective lower confidence scores.

13. The method of claim 8, wherein the dialogues stored in the database are configured to be from a series of interactions between an interactive computing system and a user of the interactive computing system.

14. The method of claim 13, wherein the series of interactions are a set of activities designed to cause an increase in a level of happiness of the user of the interactive computing system.

* * * * *